US010842818B2

(12) United States Patent
Vermeij

(10) Patent No.: US 10,842,818 B2
(45) Date of Patent: Nov. 24, 2020

(54) METHODS FOR PREPARING PLATELET PRODUCTS

(71) Applicant: Cerus Corporation, Concord, CA (US)

(72) Inventor: Johannes Vermeij, Krimpen Aan den Ljssel (NL)

(73) Assignee: Cerus Corporation, Concord, CA (US)

( * ) Notice: Subject to any disclaimer, the term of this patent is extended or adjusted under 35 U.S.C. 154(b) by 103 days.

(21) Appl. No.: 15/327,928

(22) PCT Filed: Jul. 23, 2015

(86) PCT No.: PCT/US2015/041832
§ 371 (c)(1),
(2) Date: Jan. 20, 2017

(87) PCT Pub. No.: WO2016/014854
PCT Pub. Date: Jan. 28, 2016

(65) Prior Publication Data
US 2017/0202882 A1    Jul. 20, 2017

Related U.S. Application Data

(60) Provisional application No. 62/028,245, filed on Jul. 23, 2014, provisional application No. 62/068,528, filed on Oct. 24, 2014, provisional application No. 62/185,449, filed on Jun. 26, 2015.

(51) Int. Cl.
A61K 35/19    (2015.01)
C12N 5/078    (2010.01)

(52) U.S. Cl.
CPC ............ *A61K 35/19* (2013.01); *C12N 5/0644* (2013.01)

(58) Field of Classification Search
CPC .............................. A61K 35/19; C12N 5/0644
See application file for complete search history.

(56) References Cited

U.S. PATENT DOCUMENTS

| 5,167,656 | A  | 12/1992 | Lynn |
| 5,405,343 | A  | 4/1995  | Mohr |
| 5,559,250 | A  | 9/1996  | Cook et al. |
| 5,691,132 | A  | 11/1997 | Wollowitz et al. |
| 6,093,725 | A  | 7/2000  | Cook et al. |
| 6,143,490 | A  | 11/2000 | Cook et al. |
| 6,171,777 | B1 | 1/2001  | Cook et al. |
| 6,177,441 | B1 | 1/2001  | Cook et al. |
| 6,270,952 | B1 | 8/2001  | Cook et al. |
| 6,410,219 | B1 | 6/2002  | Cook et al. |
| 6,514,987 | B1 | 2/2003  | Cook et al. |
| 6,548,242 | B2 | 4/2003  | Horowitz et al. |
| 6,709,810 | B2 | 3/2004  | Cook et al. |
| 7,025,877 | B1 | 4/2006  | De Gheldere et al. |
| 7,293,985 | B2 | 11/2007 | Cook et al. |
| 7,655,392 | B2 | 2/2010  | Stassinopoulos |
| 8,296,071 | B2 | 10/2012 | Edrich et al. |
| 8,439,889 | B2 | 5/2013  | Sano |
| 8,900,805 | B2 | 12/2014 | Mufti et al. |
| 2002/0028432 | A1 | 3/2002  | Cook et al. |
| 2002/0182581 | A1 | 12/2002 | Cook et al. |
| 2004/0029897 | A1 | 2/2004  | Cook et al. |
| 2004/0180321 | A1 | 9/2004  | Cook et al. |
| 2005/0202395 | A1 | 8/2005  | Edrich et al. |
| 2006/0115466 | A1 | 6/2006  | Stassinopoulos |
| 2011/0100919 | A1 | 5/2011  | Dorian |
| 2011/0286987 | A1 | 11/2011 | Mufti et al. |
| 2012/0111807 | A1 | 5/2012  | Hillyer et al. |
| 2012/0125847 | A1 | 5/2012  | Sehgal et al. |
| 2015/0157665 | A1 | 6/2015  | Mufti et al. |
| 2017/0202882 | A1 | 7/2017  | Johannes |

FOREIGN PATENT DOCUMENTS

| CN | 103505910 A     | 1/2014  |
| KR | 2012 0119262 A  | 10/2012 |
| WO | WO-1993/000005 A1 | 1/1993 |
| WO | WO1995019705 A1 | 7/1995  |
| WO | WO-1996/008965 A1 | 3/1996 |
| WO | WO-1996/039815 A1 | 12/1996 |
| WO | WO-1996/039820 A1 | 12/1996 |
| WO | WO-1996/040857 A1 | 12/1996 |
| WO | WO-1998/018908 A1 | 5/1998 |
| WO | WO-1998/030327 A1 | 7/1998 |
| WO | WO-1999/034914 A1 | 7/1999 |
| WO | WO-2003/049784 A2 | 6/2003 |
| WO | WO-2003/078023 A1 | 9/2003 |
| WO | WO-2003/090794 A1 | 11/2003 |
| WO | WO-2009/087560 A1 | 7/2009 |
| WO | WO-2009/117368 A2 | 9/2009 |
| WO | WO-2010/033605 A2 | 3/2010 |
| WO | WO-2010/064267 A1 | 6/2010 |
| WO | WO-2012/018484 A2 | 2/2012 |
| WO | WO-2012/071135 A2 | 5/2012 |

(Continued)

OTHER PUBLICATIONS

Van Rhenen et al., Transfusion Medicine, 1998, vol. 8, p. 319-324.*
Weibrich et al., 2001, Int. J. Oral Maxillofac. Implants, vol. 16, p. 693-699.*
Irsch et al.,Transfus. Med. Hemother., 2011, vol. 38, p. 19-31.*
Dohan et al., Oral Surg Oral Med Oral Pathol Oral Radiol Endod, 2006, vol. 101, p. E37-E44.*
"Guidance for Industry and FDA Review Staff Collection of Platelets by Automated Methods Contains Nonbinding Recommendations Table of Contents," (Dec. 1, 2007, 34 pages. Retrieved from the Internet: URL:http://www.fda.gov/downloads/BiologicsBloodVaccines/GuidanceComplianceRegulatoryInformation/Guidances/Blood/ucm862946.pdf, last visited on Aug. 24, 2015.

(Continued)

Primary Examiner — Kade Ariani
(74) Attorney, Agent, or Firm — Morrison & Foerster LLP

(57) ABSTRACT

Provided herein are improved processes for preparing and treating platelet products. The methods are useful in the efficient preparation of platelet products with desirable characteristics, including pathogen inactivated platelet products.

31 Claims, 3 Drawing Sheets

(56) References Cited

FOREIGN PATENT DOCUMENTS

| WO | WO-2012/085910 A1 | 6/2012 |
|----|-------------------|--------|
| WO | WO-2013/042095 A1 | 3/2013 |
| WO | WO2016115535 A1   | 7/2016 |

OTHER PUBLICATIONS

Holme, S. et al. (Jan. 1998). "A Multi-Laboratory Evaluation Of In Vitro Platelet Assays: The Tests For Extent Of Shape Change And Response To Hypotonic Shock, Biomedical Excellence For Safer Transfusion Working Party Of The International Society Of Blood Transfusion," *Transfusion* 38(1):31-40.

Hurtado, C. et al. "Quality Analysis of Blood Components Obtained By Automated Buffy-Coat Layer Removal With A Top & Bottom System (Optipress® II)," *Haematologica* 85(4):390-395, 2000.

Infanti, L. et al. (Jan. 1, 2011). "Pathogen-Inactivation Of Platelet Components With The Intercept Blood System™: A Cohort Study," *Transfusion and Apheresis Science*, 45(2):175-181.

Levin E. et al. (Apr. 2012). "Development Of A Quality Monitoring Program For Platelet Components: A Report Of The First Four Years' Experience At Canadian Blood Services," *Transfusion* 52(4):810-818.

Prodouz et al. (1992). "Effects Of Two Viral Inactivation Methods On Platelets: Laser-UV Radiation And Merocyanine 540-Mediated Photoinactivation," *Blood Cells* 18(1):101-114.

Sofer G. (Aug. 2002). "Virus Inactivation In the 1990s—And Into the 21$^{st}$ Century Part 2, Red Blood Cells and Platelets," *BioPharm.* pp. 42-49.

Van Rhenen, D.J. et al. (Dec. 1998). "Quality And Standardization In Blood Component Preparation With An Automated Blood Processing Technique," *Transfusion Medicine* 8(4):319-324.

Communication Article 94(3), dated Apr. 25, 2018, for EP Application No. 15747902.3, filed Feb. 20, 2017.

International Preliminary Report Patentability, dated Jan. 24, 2017 for PCT/US2015/041832, filed on Jul. 23, 2015, 17 pages.

International Search Report, dated Nov. 26, 2016, for PCT/US2015/041832, filed on Jul. 23, 2015, 9 Pages.

Invitation To Pay Additional Fees dated Oct. 2, 2015, for PCT/US2015/041832, filed Jul. 23, 2015, 113 pages.

Written Opinion Of The International Search Authority, dated Nov. 26, 2016, for PCT/US2015/041832, filed on Jul. 23, 2015, 16 pages.

"Medicare, Medicaid, and CLIA Programs; Continuing Approval of AABB (Formerly the American Association of Blood Banks as a CLIA Accreditation Organization," 73 Federal Register 101 (May 23, 2008), pp. 30109-30111.

Klein, H. G. et al. (2005). "Blood Donors and The Withdrawal of Blood," Chapter 1 in Mollison's Blood Transfusion in Clinical Medicine 11th Ed. 21 pages.

GB18469-2012 (May 11, 2012). "Quality Requirements For Whole Blood And Blood Components," National Standardization Administration Commission of the Ministry of Health of the People's Republic of China, 9 pages.

Sibinga, C.T.S. (Dec. 31, 1988). "Collection, Preparation and Preservation Of Platelet Products," Foreign Medical Sciences Sciences (Section of Blood Transfusion and Hematology), 11(3):212-213 and Machine Translation of Abstract.

* cited by examiner

Figure 1

| Volume mL | Blood | WB+CPD | 0.38 | 0.385 | 0.39 | 0.395 | 0.4 | 0.405 | 0.41 | 0.415 | 0.42 | 0.425 | 0.43 | 0.435 | 0.44 | 0.445 | 0.45 | 0.455 | 0.46 | 0.465 | 0.47 | 0.475 | 0.48 | 0.485 | 0.49 | 0.495 | 0.5 |
|---|---|---|---|---|---|---|---|---|---|---|---|---|---|---|---|---|---|---|---|---|---|---|---|---|---|---|---|
| | | | | | | | | | | | | | | Donor Hematocrit L/L | | | | | | | | | | | | | |
| | 405 | 468 | 0.329 | 0.333 | 0.338 | 0.342 | 0.346 | 0.350 | 0.355 | 0.359 | 0.363 | 0.368 | 0.372 | 0.376 | 0.381 | 0.385 | 0.389 | 0.394 | 0.398 | 0.402 | 0.407 | 0.411 | 0.415 | 0.420 | 0.424 | 0.428 | 0.433 |
| | 410 | 473 | 0.329 | 0.334 | 0.338 | 0.342 | 0.347 | 0.351 | 0.355 | 0.360 | 0.364 | 0.368 | 0.373 | 0.377 | 0.381 | 0.386 | 0.390 | 0.394 | 0.399 | 0.403 | 0.407 | 0.412 | 0.416 | 0.420 | 0.425 | 0.429 | 0.433 |
| | 415 | 478 | 0.330 | 0.334 | 0.339 | 0.343 | 0.347 | 0.352 | 0.356 | 0.360 | 0.365 | 0.369 | 0.373 | 0.378 | 0.382 | 0.386 | 0.391 | 0.395 | 0.399 | 0.404 | 0.408 | 0.412 | 0.417 | 0.421 | 0.425 | 0.430 | 0.434 |
| | 420 | 483 | 0.330 | 0.335 | 0.339 | 0.343 | 0.348 | 0.352 | 0.357 | 0.361 | 0.365 | 0.370 | 0.374 | 0.378 | 0.383 | 0.387 | 0.391 | 0.396 | 0.400 | 0.404 | 0.409 | 0.413 | 0.417 | 0.422 | 0.426 | 0.430 | 0.435 |
| | 425 | 488 | 0.331 | 0.335 | 0.340 | 0.344 | 0.348 | 0.353 | 0.357 | 0.361 | 0.366 | 0.370 | 0.374 | 0.379 | 0.383 | 0.388 | 0.392 | 0.396 | 0.401 | 0.405 | 0.409 | 0.414 | 0.418 | 0.422 | 0.427 | 0.431 | 0.435 |
| | 430 | 493 | 0.331 | 0.336 | 0.340 | 0.345 | 0.349 | 0.353 | 0.358 | 0.362 | 0.366 | 0.371 | 0.375 | 0.379 | 0.384 | 0.388 | 0.392 | 0.397 | 0.401 | 0.406 | 0.410 | 0.414 | 0.419 | 0.423 | 0.427 | 0.432 | 0.436 |
| | 435 | 498 | 0.332 | 0.336 | 0.341 | 0.345 | 0.349 | 0.354 | 0.358 | 0.363 | 0.367 | 0.371 | 0.376 | 0.380 | 0.384 | 0.389 | 0.393 | 0.397 | 0.402 | 0.406 | 0.411 | 0.415 | 0.419 | 0.424 | 0.428 | 0.432 | 0.437 |
| | 440 | 503 | 0.332 | 0.337 | 0.341 | 0.346 | 0.350 | 0.354 | 0.359 | 0.363 | 0.367 | 0.372 | 0.376 | 0.381 | 0.385 | 0.389 | 0.394 | 0.398 | 0.402 | 0.407 | 0.411 | 0.416 | 0.420 | 0.424 | 0.429 | 0.433 | 0.437 |
| | 445 | 508 | 0.333 | 0.337 | 0.342 | 0.346 | 0.350 | 0.355 | 0.359 | 0.364 | 0.368 | 0.372 | 0.377 | 0.381 | 0.385 | 0.390 | 0.394 | 0.399 | 0.403 | 0.407 | 0.412 | 0.416 | 0.420 | 0.425 | 0.429 | 0.434 | 0.438 |
| | 450 | 513 | 0.333 | 0.338 | 0.342 | 0.346 | 0.351 | 0.355 | 0.360 | 0.364 | 0.368 | 0.373 | 0.377 | 0.382 | 0.386 | 0.390 | 0.395 | 0.399 | 0.404 | 0.408 | 0.412 | 0.417 | 0.421 | 0.425 | 0.430 | 0.434 | 0.439 |
| | 455 | 518 | 0.334 | 0.338 | 0.343 | 0.347 | 0.351 | 0.356 | 0.360 | 0.365 | 0.369 | 0.373 | 0.378 | 0.382 | 0.386 | 0.391 | 0.395 | 0.400 | 0.404 | 0.408 | 0.413 | 0.417 | 0.422 | 0.426 | 0.430 | 0.435 | 0.439 |
| | 460 | 523 | 0.334 | 0.339 | 0.343 | 0.347 | 0.352 | 0.356 | 0.361 | 0.365 | 0.369 | 0.374 | 0.378 | 0.383 | 0.387 | 0.391 | 0.396 | 0.400 | 0.405 | 0.409 | 0.413 | 0.418 | 0.422 | 0.427 | 0.431 | 0.435 | 0.440 |
| | 465 | 528 | 0.335 | 0.339 | 0.343 | 0.348 | 0.352 | 0.357 | 0.361 | 0.365 | 0.370 | 0.374 | 0.379 | 0.383 | 0.388 | 0.392 | 0.396 | 0.401 | 0.405 | 0.410 | 0.414 | 0.418 | 0.423 | 0.427 | 0.432 | 0.436 | 0.440 |
| | 470 | 533 | 0.335 | 0.339 | 0.344 | 0.348 | 0.353 | 0.357 | 0.362 | 0.366 | 0.370 | 0.375 | 0.379 | 0.384 | 0.388 | 0.392 | 0.397 | 0.401 | 0.406 | 0.410 | 0.414 | 0.419 | 0.423 | 0.428 | 0.432 | 0.436 | 0.441 |
| | 475 | 538 | 0.336 | 0.340 | 0.344 | 0.349 | 0.353 | 0.358 | 0.362 | 0.366 | 0.371 | 0.375 | 0.380 | 0.384 | 0.388 | 0.393 | 0.397 | 0.402 | 0.406 | 0.411 | 0.415 | 0.419 | 0.424 | 0.428 | 0.433 | 0.437 | 0.441 |
| | 480 | 543 | 0.336 | 0.340 | 0.345 | 0.349 | 0.354 | 0.358 | 0.362 | 0.367 | 0.371 | 0.376 | 0.380 | 0.385 | 0.389 | 0.393 | 0.398 | 0.402 | 0.407 | 0.411 | 0.415 | 0.420 | 0.424 | 0.429 | 0.433 | 0.438 | 0.442 |
| | 485 | 548 | 0.336 | 0.341 | 0.345 | 0.350 | 0.354 | 0.358 | 0.363 | 0.367 | 0.372 | 0.376 | 0.381 | 0.385 | 0.389 | 0.394 | 0.398 | 0.403 | 0.407 | 0.412 | 0.416 | 0.420 | 0.425 | 0.429 | 0.434 | 0.438 | 0.443 |
| | 490 | 553 | 0.337 | 0.341 | 0.346 | 0.350 | 0.354 | 0.359 | 0.363 | 0.368 | 0.372 | 0.377 | 0.381 | 0.385 | 0.390 | 0.394 | 0.399 | 0.403 | 0.408 | 0.412 | 0.416 | 0.421 | 0.425 | 0.430 | 0.434 | 0.439 | 0.443 |
| | 495 | 558 | 0.337 | 0.342 | 0.346 | 0.350 | 0.355 | 0.359 | 0.364 | 0.368 | 0.373 | 0.377 | 0.381 | 0.386 | 0.390 | 0.395 | 0.399 | 0.404 | 0.408 | 0.413 | 0.417 | 0.421 | 0.426 | 0.430 | 0.435 | 0.439 | 0.444 |

Figure 2

| Volume mL | | Donor Hematocrit L/L | | | | | | | | | | | | | | | | | | | | | | | | |
|---|---|---|---|---|---|---|---|---|---|---|---|---|---|---|---|---|---|---|---|---|---|---|---|---|---|---|
| Blood | WB+CPD | 0.38 | 0.385 | 0.39 | 0.395 | 0.4 | 0.405 | 0.41 | 0.415 | 0.42 | 0.425 | 0.43 | 0.435 | 0.44 | 0.445 | 0.45 | 0.455 | 0.46 | 0.465 | 0.47 | 0.475 | 0.48 | 0.485 | 0.49 | 0.495 | 0.5 |
| 405 | 468 | 0.329 | 0.333 | 0.338 | 0.342 | 0.346 | 0.350 | 0.355 | 0.359 | 0.363 | 0.368 | 0.372 | 0.376 | 0.381 | 0.385 | 0.389 | 0.394 | 0.398 | 0.402 | 0.407 | 0.411 | 0.415 | 0.420 | 0.424 | 0.428 | 0.433 |
| 410 | 473 | 0.329 | 0.334 | 0.338 | 0.342 | 0.347 | 0.351 | 0.355 | 0.360 | 0.364 | 0.368 | 0.373 | 0.377 | 0.381 | 0.386 | 0.390 | 0.394 | 0.399 | 0.403 | 0.407 | 0.412 | 0.416 | 0.420 | 0.425 | 0.429 | 0.433 |
| 415 | 478 | 0.330 | 0.334 | 0.339 | 0.343 | 0.347 | 0.352 | 0.356 | 0.360 | 0.365 | 0.369 | 0.373 | 0.378 | 0.382 | 0.386 | 0.391 | 0.395 | 0.399 | 0.404 | 0.408 | 0.412 | 0.417 | 0.421 | 0.425 | 0.430 | 0.434 |
| 420 | 483 | 0.330 | 0.335 | 0.339 | 0.343 | 0.348 | 0.352 | 0.357 | 0.361 | 0.365 | 0.370 | 0.374 | 0.378 | 0.383 | 0.387 | 0.391 | 0.396 | 0.400 | 0.404 | 0.409 | 0.413 | 0.417 | 0.422 | 0.426 | 0.430 | 0.435 |
| 425 | 488 | 0.331 | 0.335 | 0.340 | 0.344 | 0.348 | 0.353 | 0.357 | 0.361 | 0.366 | 0.370 | 0.374 | 0.379 | 0.383 | 0.388 | 0.392 | 0.396 | 0.401 | 0.405 | 0.409 | 0.414 | 0.418 | 0.422 | 0.427 | 0.431 | 0.435 |
| 430 | 493 | 0.331 | 0.336 | 0.340 | 0.344 | 0.349 | 0.353 | 0.358 | 0.362 | 0.366 | 0.371 | 0.375 | 0.379 | 0.384 | 0.388 | 0.392 | 0.397 | 0.401 | 0.406 | 0.410 | 0.414 | 0.419 | 0.423 | 0.427 | 0.432 | 0.436 |
| 435 | 498 | 0.332 | 0.336 | 0.341 | 0.345 | 0.349 | 0.354 | 0.358 | 0.363 | 0.367 | 0.371 | 0.376 | 0.380 | 0.384 | 0.389 | 0.393 | 0.397 | 0.402 | 0.406 | 0.411 | 0.415 | 0.419 | 0.424 | 0.428 | 0.432 | 0.437 |
| 440 | 503 | 0.332 | 0.337 | 0.341 | 0.345 | 0.350 | 0.354 | 0.358 | 0.363 | 0.367 | 0.372 | 0.376 | 0.381 | 0.385 | 0.389 | 0.394 | 0.398 | 0.402 | 0.407 | 0.411 | 0.416 | 0.420 | 0.424 | 0.429 | 0.433 | 0.437 |
| 445 | 508 | 0.333 | 0.337 | 0.342 | 0.346 | 0.350 | 0.355 | 0.359 | 0.363 | 0.368 | 0.372 | 0.377 | 0.381 | 0.385 | 0.390 | 0.394 | 0.399 | 0.403 | 0.407 | 0.412 | 0.416 | 0.420 | 0.425 | 0.429 | 0.434 | 0.438 |
| 450 | 513 | 0.333 | 0.338 | 0.342 | 0.346 | 0.351 | 0.355 | 0.360 | 0.364 | 0.368 | 0.373 | 0.377 | 0.382 | 0.386 | 0.390 | 0.395 | 0.399 | 0.404 | 0.408 | 0.412 | 0.417 | 0.421 | 0.425 | 0.430 | 0.434 | 0.439 |
| 455 | 518 | 0.334 | 0.338 | 0.343 | 0.347 | 0.351 | 0.356 | 0.360 | 0.365 | 0.369 | 0.373 | 0.378 | 0.382 | 0.386 | 0.391 | 0.395 | 0.400 | 0.404 | 0.408 | 0.413 | 0.417 | 0.422 | 0.426 | 0.430 | 0.435 | 0.439 |
| 460 | 523 | 0.334 | 0.339 | 0.343 | 0.347 | 0.352 | 0.356 | 0.361 | 0.365 | 0.369 | 0.374 | 0.378 | 0.383 | 0.387 | 0.391 | 0.396 | 0.400 | 0.405 | 0.409 | 0.413 | 0.418 | 0.422 | 0.427 | 0.431 | 0.435 | 0.440 |
| 465 | 528 | 0.335 | 0.339 | 0.343 | 0.348 | 0.352 | 0.357 | 0.361 | 0.365 | 0.370 | 0.374 | 0.379 | 0.383 | 0.388 | 0.392 | 0.396 | 0.401 | 0.405 | 0.410 | 0.414 | 0.418 | 0.423 | 0.427 | 0.432 | 0.436 | 0.440 |
| 470 | 533 | 0.335 | 0.339 | 0.344 | 0.348 | 0.353 | 0.357 | 0.362 | 0.366 | 0.370 | 0.375 | 0.379 | 0.384 | 0.388 | 0.392 | 0.397 | 0.401 | 0.406 | 0.410 | 0.414 | 0.419 | 0.423 | 0.428 | 0.432 | 0.436 | 0.441 |
| 475 | 538 | 0.336 | 0.340 | 0.344 | 0.349 | 0.353 | 0.358 | 0.362 | 0.366 | 0.371 | 0.375 | 0.380 | 0.384 | 0.388 | 0.393 | 0.397 | 0.402 | 0.406 | 0.411 | 0.415 | 0.419 | 0.424 | 0.428 | 0.433 | 0.437 | 0.441 |
| 480 | 543 | 0.336 | 0.340 | 0.345 | 0.349 | 0.354 | 0.358 | 0.362 | 0.367 | 0.371 | 0.376 | 0.380 | 0.385 | 0.389 | 0.393 | 0.398 | 0.402 | 0.407 | 0.411 | 0.415 | 0.420 | 0.424 | 0.429 | 0.433 | 0.438 | 0.442 |
| 485 | 548 | 0.336 | 0.341 | 0.345 | 0.350 | 0.354 | 0.358 | 0.363 | 0.367 | 0.372 | 0.376 | 0.381 | 0.385 | 0.389 | 0.394 | 0.398 | 0.403 | 0.407 | 0.412 | 0.416 | 0.420 | 0.425 | 0.429 | 0.434 | 0.438 | 0.443 |
| 490 | 553 | 0.337 | 0.341 | 0.346 | 0.350 | 0.354 | 0.359 | 0.363 | 0.368 | 0.372 | 0.377 | 0.381 | 0.385 | 0.390 | 0.394 | 0.399 | 0.403 | 0.408 | 0.412 | 0.416 | 0.421 | 0.425 | 0.430 | 0.434 | 0.439 | 0.443 |
| 495 | 558 | 0.337 | 0.342 | 0.346 | 0.350 | 0.355 | 0.359 | 0.364 | 0.368 | 0.373 | 0.377 | 0.381 | 0.386 | 0.390 | 0.395 | 0.399 | 0.404 | 0.408 | 0.413 | 0.417 | 0.421 | 0.426 | 0.430 | 0.435 | 0.439 | 0.444 |

Figure 3

| Volume ml | | Donor Hematocrit L/L | | | | | | | | | | | | | | | | | | | | | | | | |
|---|---|---|---|---|---|---|---|---|---|---|---|---|---|---|---|---|---|---|---|---|---|---|---|---|---|---|
| Blood | WB+CPD | 0.38 | 0.385 | 0.39 | 0.395 | 0.4 | 0.405 | 0.41 | 0.415 | 0.42 | 0.425 | 0.43 | 0.435 | 0.44 | 0.445 | 0.45 | 0.455 | 0.46 | 0.465 | 0.47 | 0.475 | 0.48 | 0.485 | 0.49 | 0.495 | 0.5 |
| 405 | 468 | 0.329 | 0.333 | 0.338 | 0.342 | 0.346 | 0.350 | 0.355 | 0.359 | 0.363 | 0.368 | 0.372 | 0.376 | 0.381 | 0.385 | 0.389 | 0.394 | 0.398 | 0.402 | 0.407 | 0.411 | 0.415 | 0.420 | 0.424 | 0.428 | 0.433 |
| 410 | 473 | 0.329 | 0.334 | 0.338 | 0.342 | 0.347 | 0.351 | 0.355 | 0.360 | 0.364 | 0.368 | 0.373 | 0.377 | 0.381 | 0.386 | 0.390 | 0.394 | 0.399 | 0.403 | 0.407 | 0.412 | 0.416 | 0.420 | 0.425 | 0.429 | 0.433 |
| 415 | 478 | 0.330 | 0.334 | 0.339 | 0.343 | 0.347 | 0.352 | 0.356 | 0.360 | 0.365 | 0.369 | 0.373 | 0.378 | 0.382 | 0.386 | 0.391 | 0.395 | 0.399 | 0.404 | 0.408 | 0.412 | 0.417 | 0.421 | 0.425 | 0.430 | 0.434 |
| 420 | 483 | 0.330 | 0.335 | 0.339 | 0.343 | 0.348 | 0.352 | 0.357 | 0.361 | 0.365 | 0.370 | 0.374 | 0.378 | 0.383 | 0.387 | 0.391 | 0.396 | 0.400 | 0.404 | 0.409 | 0.413 | 0.417 | 0.422 | 0.426 | 0.430 | 0.435 |
| 425 | 488 | 0.331 | 0.335 | 0.340 | 0.344 | 0.348 | 0.353 | 0.357 | 0.361 | 0.366 | 0.370 | 0.374 | 0.379 | 0.383 | 0.388 | 0.392 | 0.396 | 0.401 | 0.405 | 0.409 | 0.414 | 0.418 | 0.422 | 0.427 | 0.431 | 0.435 |
| 430 | 493 | 0.331 | 0.336 | 0.340 | 0.345 | 0.349 | 0.353 | 0.358 | 0.362 | 0.366 | 0.371 | 0.375 | 0.379 | 0.384 | 0.388 | 0.392 | 0.397 | 0.401 | 0.406 | 0.410 | 0.414 | 0.419 | 0.423 | 0.427 | 0.432 | 0.436 |
| 435 | 498 | 0.332 | 0.336 | 0.341 | 0.345 | 0.349 | 0.354 | 0.358 | 0.363 | 0.367 | 0.371 | 0.376 | 0.380 | 0.384 | 0.389 | 0.393 | 0.397 | 0.402 | 0.406 | 0.411 | 0.415 | 0.419 | 0.424 | 0.428 | 0.432 | 0.437 |
| 440 | 503 | 0.332 | 0.337 | 0.341 | 0.346 | 0.350 | 0.354 | 0.359 | 0.363 | 0.367 | 0.372 | 0.376 | 0.381 | 0.385 | 0.389 | 0.394 | 0.398 | 0.402 | 0.407 | 0.411 | 0.416 | 0.420 | 0.424 | 0.429 | 0.433 | 0.437 |
| 445 | 508 | 0.333 | 0.337 | 0.342 | 0.346 | 0.350 | 0.355 | 0.359 | 0.364 | 0.368 | 0.372 | 0.377 | 0.381 | 0.385 | 0.390 | 0.394 | 0.399 | 0.403 | 0.407 | 0.412 | 0.416 | 0.420 | 0.425 | 0.429 | 0.434 | 0.438 |
| 450 | 513 | 0.333 | 0.338 | 0.342 | 0.346 | 0.351 | 0.355 | 0.360 | 0.364 | 0.368 | 0.373 | 0.377 | 0.382 | 0.386 | 0.390 | 0.395 | 0.399 | 0.404 | 0.408 | 0.412 | 0.417 | 0.421 | 0.425 | 0.430 | 0.434 | 0.439 |
| 455 | 518 | 0.334 | 0.338 | 0.343 | 0.347 | 0.351 | 0.356 | 0.360 | 0.365 | 0.369 | 0.373 | 0.378 | 0.382 | 0.386 | 0.391 | 0.395 | 0.400 | 0.404 | 0.408 | 0.413 | 0.417 | 0.422 | 0.426 | 0.430 | 0.435 | 0.439 |
| 460 | 523 | 0.334 | 0.339 | 0.343 | 0.347 | 0.352 | 0.356 | 0.361 | 0.365 | 0.369 | 0.374 | 0.378 | 0.383 | 0.387 | 0.391 | 0.396 | 0.400 | 0.405 | 0.409 | 0.413 | 0.418 | 0.422 | 0.427 | 0.431 | 0.435 | 0.440 |
| 465 | 528 | 0.335 | 0.339 | 0.343 | 0.348 | 0.352 | 0.357 | 0.361 | 0.365 | 0.370 | 0.374 | 0.379 | 0.383 | 0.388 | 0.392 | 0.396 | 0.401 | 0.405 | 0.410 | 0.414 | 0.418 | 0.423 | 0.427 | 0.432 | 0.436 | 0.440 |
| 470 | 533 | 0.335 | 0.339 | 0.344 | 0.348 | 0.353 | 0.357 | 0.362 | 0.366 | 0.370 | 0.375 | 0.379 | 0.384 | 0.388 | 0.392 | 0.397 | 0.401 | 0.406 | 0.410 | 0.414 | 0.419 | 0.423 | 0.428 | 0.432 | 0.436 | 0.441 |
| 475 | 538 | 0.336 | 0.340 | 0.344 | 0.349 | 0.353 | 0.358 | 0.362 | 0.366 | 0.371 | 0.375 | 0.380 | 0.384 | 0.388 | 0.393 | 0.397 | 0.402 | 0.406 | 0.411 | 0.415 | 0.419 | 0.424 | 0.428 | 0.433 | 0.437 | 0.441 |
| 480 | 543 | 0.336 | 0.340 | 0.345 | 0.349 | 0.354 | 0.358 | 0.362 | 0.367 | 0.371 | 0.376 | 0.380 | 0.385 | 0.389 | 0.393 | 0.398 | 0.402 | 0.407 | 0.411 | 0.415 | 0.420 | 0.424 | 0.429 | 0.433 | 0.438 | 0.442 |
| 485 | 548 | 0.336 | 0.341 | 0.345 | 0.350 | 0.354 | 0.358 | 0.363 | 0.367 | 0.372 | 0.376 | 0.381 | 0.385 | 0.389 | 0.394 | 0.398 | 0.403 | 0.407 | 0.412 | 0.416 | 0.420 | 0.425 | 0.429 | 0.434 | 0.438 | 0.443 |
| 490 | 553 | 0.337 | 0.341 | 0.346 | 0.350 | 0.354 | 0.359 | 0.363 | 0.368 | 0.372 | 0.377 | 0.381 | 0.385 | 0.390 | 0.394 | 0.399 | 0.403 | 0.408 | 0.412 | 0.416 | 0.421 | 0.425 | 0.430 | 0.434 | 0.439 | 0.443 |
| 495 | 558 | 0.337 | 0.342 | 0.346 | 0.350 | 0.355 | 0.359 | 0.364 | 0.368 | 0.373 | 0.377 | 0.381 | 0.386 | 0.390 | 0.395 | 0.399 | 0.404 | 0.408 | 0.413 | 0.417 | 0.421 | 0.426 | 0.430 | 0.435 | 0.439 | 0.444 |

METHODS FOR PREPARING PLATELET PRODUCTS

CROSS REFERENCE TO RELATED APPLICATIONS

This application is a U.S. National Stage Entry of International Application No. PCT/US2015/041832 filed Jul. 23, 2015, which claims the benefit of priority of U.S. provisional patent application Ser. No. 62/028,245, filed Jul. 23, 2014; U.S. provisional patent application Ser. No. 62/068,528, filed Oct. 24, 2014; and U.S. provisional patent application Ser. No. 62/185,449, filed Jun. 26, 2015, the contents of each of which are hereby incorporated by reference herein in their entirety.

FIELD OF THE INVENTION

The methods described herein generally relate to the preparation of platelet-containing blood products. More particularly, the present disclosure relates to improved methods for preparing and treating platelet products, which may be used for transfusions.

BACKGROUND OF THE INVENTION

Blood collection and processing serves a critical role in healthcare worldwide, and millions of units of donated whole blood are collected by blood banks each year. While some whole blood units collected from donors are stored and used for transfusion, most whole blood is instead separated into its clinically therapeutic components of red blood cells, platelets and plasma, for individual storage and use in treating different medical needs and conditions requiring one or more of the particular blood components.

Platelets (also referred to as thrombocytes) play key roles in hemostasis, clot stability and retraction, as well as in vascular repair and anti-microbial host defense. A variety of methods are used to collect and store platelets to provide platelet-containing blood products. For example, the United States uses primarily apheresis collection to provide a platelet unit from a single donor, as well as platelet concentrates obtained by isolating platelet rich plasma (PRP) from standard whole blood donations, which can be pooled with platelet concentrates from one or more other donors to generate a platelet unit. Some countries, including European countries, Australia and Canada, use a process of buffy coat preparation to isolate platelets from donated blood to generate a platelet concentrate. These also are typically pooled with platelets from one or more other donors. In general for pooled platelets, platelet concentrates from four to six individual donors are combined to produce a single transfusion unit, with the platelet concentrates matched for compatible blood types.

The PRP method is one of the basic whole blood separation techniques for the preparation of blood products, including red blood cells, plasma and random donor platelets (RDP), for transfusion therapy. The RDP unit generally contains a majority of the original whole blood platelet content and is suspended in plasma. According to the European guide to the preparation, use and quality assurance of blood components, an RDP unit should contain >60×10$^9$ platelets and <0.2×10$^9$ white blood cell (WBC) in a volume of >40 mL per 60×10$^9$ platelets. While one RDP unit can be used for neonatal and infant transfusion, a standard adult transfusion dose generally requires at least 4-6 RDP units, depending on the recovery and whether or not the platelet units will be subjected to further processing (e.g., pathogen inactivation). The RDP units can be pooled prior to storage, filtered (e.g., leukoreduced) to reduce the WBC content (e.g., to <1×10$^6$) and stored for 5 to 7 days in conjunction with appropriate pathogen detection and/or pathogen inactivation treatment to reduce contamination risk.

The PRP method is based on two centrifugation steps; a first, slower "soft" spin centrifugation to separate the plasma and platelet (platelet rich plasma) components from the red blood cell component, and a second, faster "hard" spin centrifugation to concentrate the platelets and remove the excess of plasma (platelet poor plasma) to a desired remaining volume. Generally, blood banks optimize and standardize their protocols to yield the highest quality products at the lowest possible cost (e.g., shortest procedure/operator time), and the centrifugation conditions are currently standardized without consideration to individual whole blood units. For example, the widely accepted AABB technical manual (18$^{th}$ edition, 2014) instructs as a starting point a first "light" centrifugation of whole blood consisting of 2000×g for 3 minutes (plus deceleration time), followed by a "heavy" spin using 5000×g for 5-7 minutes (plus deceleration time), with calculation of relative centrifugal force (RCF) in g for a particular centrifuge model given in the formula below.

$$RCF = 28.38 \times R \times (RPM/1000)^2 \text{ or}$$

$$RPM = \sqrt{[RCF/(28.38 \times R)]} \times 1000$$

where:
RCF=relative centrifugal force (×g)
R=radius in inches
RPM=revolutions per minute While individual blood banks may further optimize centrifugation conditions for their own operating procedures, the conditions are applied without consideration to differences among individual whole blood units. In practice, this results in a high degree of process variability for the PRP method, which often results in up to about 10% or more of units being of unacceptable quality, due to any of several factors, such as for example, contamination by red blood cells, white blood cells, platelet aggregates and/or lipids, as well as variable platelet dose to lower than desirable recovery of platelets at yields of about 60-80%, which may also adversely impact the efficiency of pooling processes by requiring additional input units, with corresponding increased processing time, materials and expense. Additionally, this high degree of variability from the PRP method, may also adversely affect the treatment of platelet preparations (e.g., platelet concentrates) in subsequent pathogen inactivation methods, which may have strict process requirements.

Thus there remains a need for improved methods for preparing platelet products for transfusion and other uses, including platelet products that will be subjected to pathogen inactivation processes. Such improved methods may provide for greater efficiencies in platelet preparation, such as for example, increased platelet yields, increased numbers of product units, decreased production costs, less wastage, and/or access to a larger available donor population.

SUMMARY OF THE INVENTION

The methods described herein provide improved processes for preparing and treating platelet products, such as for example, platelet products which may be used for transfusions. The methods are useful in the efficient preparation of platelet products with desirable characteristics, including pathogen inactivated platelet products.

In one aspect, the present disclosure provides a method of preparing a platelet product comprising: a) selecting a subset of whole blood units from a plurality of donated whole blood units, wherein the plurality of donated whole blood units meet the acceptance criteria of a regulatory agency or accrediting organization for donated whole blood, wherein each unit of the subset of whole blood units is within a specified range for each of one or more parameters selected from the group consisting of hematocrit, hemoglobin, donor gender, whole blood volume, packed cell volume and platelet count, and wherein the specified range for each of the one or more parameters for the selected subset of whole blood units is narrower than the range that meets the acceptance criteria of the regulatory agency or accrediting organization for the same parameter for donated whole blood; b) centrifuging the selected subset of units under the same centrifugation conditions to provide each unit having a separated layer of platelet rich plasma; and c) isolating the separated layer of platelet rich plasma to provide a platelet rich plasma unit. In some embodiments, the one or more parameters may further comprise donor age, whole blood storage time prior to processing (e.g., prior to initiating the method), blood bag size and/or donor history of platelet aggregation. In some embodiments, the one or more parameters include hematocrit. In some embodiments, the specified range for hematocrit in the selected subset of units is about 0.400 to about 0.480 L/L, about 0.400 to about 0.470 L/L, about 0.410 to about 0.480 L/L, about 0.380 L/L to about 0.435 L/L, about 0.435 L/L to about 0.500 L/L, about 0.440 L/L to about 0.500 L/L, about 0.380 L/L to about 0.420 L/L, about 0.420 L/L to about 0.460 L/L, about 0.425 L/L to about 0.460 L/L, about 0.460 L/L to about 0.500 L/L, or about 0.465 L/L to about 0.500 L/L. In some embodiments, the specified range for hematocrit in the selected subset of units is at least about 0.380 L/L and less than about 0.435 L/L, or at least about 0.435 L/L and less than about 0.500 L/L, or greater than about 0.435 L/L and less than about 0.500 L/L, or greater than about 0.435 L/L to about 0.500 L/L. In some embodiments, the specified range for hematocrit in the selected subset of units is at least about 0.380 L/L and less than about 0.435 L/L, or at least about 0.435 L/L and less than about 0.500 L/L. Hematocrit may also be represented as a percentage. In some embodiments, the specified range for hematocrit in the selected subset of units is about 40.0% to about 48.0%, about 40.0% to about 47.0%, about 41.0% to about 48.0%, about 38.0% to about 43.5%, about 43.5% to about 50.0%, about 44.0% to about 50.0%, about 38.0% to about 42.0%, about 42.0% to about 46.0%, about 42.5% to about 46.0%, about 46.0% to about 50.0%, or about 46.5% to about 50.0%. In some embodiments, the specified range for hematocrit in the selected subset of units is at least about 38.0% and less than about 43.5%, or at least about 43.5% and less than about 50.0%, or greater than about 43.5% and less than about 50.0%, or greater than about 43.5% to about 50.0%. In some embodiments, the one or more parameters include hemoglobin. In some embodiments, the specified range for hemoglobin in the selected subset of units is about 7.8-9.4 mmol/L, about 9.4-11.0 mmol/L, about 7.8-8.9 mmol, about 8.4-9.3 mmol, about 8.9-9.9 mmol/L, about 9.0-9.9 mmol, about 9.3-10.3 mmol, about 9.4-10.2 mmol, about 9.5-11.0 mmol/L, about 9.9-11.0 mmol/L, or about 10.0-11.0 mmol. In some embodiments, the specified range for hemoglobin in the selected subset of units is about 13.5 g/dL to about 15.0 g/dL, about 15.1 g/dL to about 16.5 g/dL, or about 15.0 g/dL to about 16.5 g/dL. In some embodiments, the one or more parameters include donor gender. In some embodiments the specified range for donor gender in the selected subset of units is 100% female donors. In some embodiments, the specified range for donor gender in the selected subset of units is 100% male donors. In some embodiments, the specified range for donor gender is no more than one unit from a male donor together with the remaining units being from female donors. In some embodiments, the specified range for donor gender is no more than one unit from a female donor together with the remaining units being from male donors. In some embodiments the specified range for donor gender in the selected subset of units is one female donor for every three, every four, every five, every six or every seven male donors. In some embodiments the specified range for donor gender in the selected subset of units is one male donor for every three, every four, every five, every six, or every seven male donors. In some embodiments, the one or more parameters include whole blood volume. In some embodiments, the specified range for whole blood volume is about 270-330 mL, about 315-385 mL, about 332-368 mL, about 360-440 mL, about 405-495 mL, about 405-490 mL, about 405-450 mL, about 405-435 mL, about 427-473 mL, about 430-480 mL, about 435-465 mL, about 450-550 mL, about 450-500 mL, about 450-495 mL, about 465-495 mL, or about 475-525 mL. In some embodiments, the one or more parameters include packed cell volume. In some embodiments, the specified range for packed cell volume (e.g., fraction packed cell volume) in the selected subset of units is about 0.40 to about 0.48, about 0.40 to about 0.47, about 0.41 to about 0.48, about 0.38 to about 0.44, about 0.44 to about 0.50, about 0.38 to about 0.42, about 0.42 to about 0.46, or about 0.46 to about 0.50. In some embodiments, the one or more parameters include platelet count. In some embodiments, each unit of the selected subset of whole blood units is within the same specified range for two or more of the aforementioned parameters. In some embodiments, the two or more parameters include hematocrit and hemoglobin, hematocrit and donor gender, hematocrit and whole blood volume, hematocrit and packed cell volume or hematocrit and platelet count. In some embodiments, the two or more parameters include hemoglobin and donor gender, hemoglobin and whole blood volume, hemoglobin and packed cell volume or hemoglobin and platelet count. In some embodiments, the two or more parameters include donor gender and whole blood volume, donor gender and packed cell volume or donor gender and platelet count. In some embodiments, the two or more parameters include whole blood volume and packed cell volume or whole blood volume and platelet count. In some embodiments, the two or more parameters include packed cell volume and platelet count. In some embodiments, each unit of the selected subset of whole blood units is within the same specified range for three or more of the aforementioned parameters. In some embodiments, the three or more parameters include hematocrit, hemoglobin and donor gender. In some embodiments, the three or more parameters include hematocrit, hemoglobin and whole blood volume. In some embodiments, the three or more parameters include hematocrit, hemoglobin and packed cell volume. In some embodiments, the three or more parameters include hematocrit, hemoglobin and platelet count. In some embodiments, the three or more parameters include hematocrit, donor gender and whole blood volume. In some embodiments, the three or more parameters include hematocrit, donor gender and packed cell volume. In some embodiments, the three or more parameters include hematocrit, donor gender and platelet count. In some embodiments, the three or more parameters include hematocrit, whole blood volume and packed cell volume. In some embodiments, the three or more parameters include hematocrit, whole blood volume and platelet count. In some embodiments, the three or more parameters include hematocrit, packed cell volume and platelet count. In some embodiments, the three or more parameters include hemoglobin, donor gender and whole blood volume. In some embodiments, the three or more parameters include hemoglobin, donor gender and packed cell volume. In some embodiments, the three or more parameters include hemoglobin, donor gender and platelet count. In some embodiments, the three or more parameters include hemoglobin, whole blood volume and packed cell volume. In some embodiments, the three or more parameters include hemoglobin, whole blood volume and platelet count. In some embodiments, the three or more parameters include hemoglobin, packed cell volume and platelet count. In some embodiments, the three or more parameters include donor gender, whole blood volume and packed cell volume. In some embodiments, the three or more parameters include donor gender, whole blood volume and platelet count. In some embodiments, the three or more parameters include donor gender, packed cell volume and platelet count. In some embodiments, the three or more parameters include whole blood volume, packed cell volume and platelet count. In some embodiments, each unit of the subset of whole blood units is within the same specified range for four or more, or five or more of the aforementioned parameters. In some embodiments of the aforementioned methods, the specified range for each of the one or more parameters for the selected subset of whole blood units is narrower than the range for the same parameter in the plurality of donated whole blood units.

In some embodiments of the aforementioned methods, each unit of the selected subset of whole blood units is within one of at least two specified ranges for at least one of the one or more parameters. In some embodiments, each of the at least two specified ranges for at least one of the one or more parameters for the selected subset of whole blood units is narrower than the range that meets the acceptance criteria of a regulatory agency or accrediting organization for the same parameter for donated whole blood. In some embodiments, at least one of the one or more parameters is whole blood volume, and the at least two specified ranges include 405-450 mL and 451-495 mL. In some embodiments, at least one of the one or more parameters is whole blood volume, and the at least two specified ranges include 405-450 mL and 450-495 mL. In some embodiments, at least one of the one or more parameters is hematocrit, and the at least two specified ranges include about 0.380 L/L to about 0.435 L/L and about 0.440 L/L to about 0.500 L/L. In some embodiments, at least one of the one or more parameters is hematocrit, and the at least two specified ranges include about 0.380 L/L to about 0.435 L/L and about 0.435 L/L to about 0.500 L/L. In some embodiments, at least one of the one or more parameters is hemoglobin, and the at least two specified ranges include 7.8-9.4 mmol/L and 9.5-11.0 mmol/L. In some embodiments, at least one of the one or more parameters is hemoglobin, and the at least two specified ranges include 7.8-9.4 mmol/L and 9.4-11.0 mmol/L. In some embodiments, at least one of the one or more parameters is hemoglobin, and the at least two specified ranges include about 13.5 g/dL to about 15.0 g/dL and about 15.1 g/dL to about 16.5 g/dL. In some embodiments, at least one of the one or more parameters is hemoglobin, and the at least two specified ranges include about 13.5 g/dL to about 15.0 g/dL and about 15.0 g/dL to about 16.5 g/dL. In some embodiments of the aforementioned methods, the method further comprises selecting a first subset of whole blood units within a first specified range of the at least two specified ranges and selecting a second subset of whole blood units within a second specified range of the at least two specified ranges for at least one of the one or more parameters. In some embodiments, the method further comprises centrifuging the first selected subset of whole blood units and the second selected subset of whole blood units under different centrifugation conditions. In some embodiments, the centrifugation conditions are determined by each of the at least two specified ranges for the one or more parameters. In some embodiments, the centrifugation conditions determined for each of the at least two specified ranges for the one or more parameters are different from each other. In some embodiments, the at least two specified ranges for the one or more parameters are non-overlapping ranges. In some embodiments, the at least two specified ranges for the one or more parameter are overlapping ranges (e.g., overlap by an end point of the ranges, overlap by about 1%, overlap by about 2%, overlap by about 3%). In some embodiments, each unit of the subset of whole blood units is within one of at least three specified ranges for at least one of the one or more parameters. In some embodiments, at least one of the one or more parameters is whole blood volume, and the at least three specified ranges include 405-435 mL, 436-465 mL and 466-495 mL. In some embodiments, at least one of the one or more parameters is whole blood volume, and the at least three specified ranges include 405-435 mL, 435-465 mL and 465-495 mL. In some embodiments, at least one of the one or more parameters is hematocrit, and the at least three specified ranges include about 0.380 L/L to about 0.420 L/L, about 0.425 L/L to about 0.460 L/L, and about 0.465 L/L to about 0.500 L/L. In some embodiments, at least one of the one or more parameters is hematocrit, and the at least three specified ranges include about 0.380 L/L to about 0.420 L/L, about 0.420 L/L to about 0.460 L/L, and about 0.460 L/L to about 0.500 L/L. In some embodiments, at least one of the one or more parameters is hemoglobin, and the at least three specified ranges include 7.8-8.9 mmol/L, 9.0-9.9 mmol/L and 10.0-11.0 mmol/L. In some embodiments, at least one of the one or more parameters is hemoglobin, and the at least three specified ranges include 7.8-8.9 mmol/L, 8.9-9.9 mmol/L and 9.9-11.0 mmol/L. In some embodiments, each unit of the subset of whole blood units is within one of the at least four specified ranges for at least one of the one or more parameters.

In some of the aforementioned methods, the regulatory agency is the U.S. Food and Drug Administration (FDA), the European Medicines Agency (EMA), the Australian Therapeutic Goods Administration (TGA), the China Food and Drug Administration (CFDA), or the Japan Ministry of Health, Labour, and Welfare (MHLW). In some of the aforementioned methods, the accrediting organization is the AABB or the European Directorate for the Quality of Medicines & HealthCare (EDQM).

In some of the aforementioned methods, the isolated platelet rich plasma unit comprises less than about $5 \times 10^6$ red blood cells. In some of the aforementioned methods, the method further comprises processing the isolated platelet rich plasma unit to provide a platelet rich plasma unit for pathogen inactivation. In some of the aforementioned methods, the method further comprises: d) centrifuging the isolated platelet rich plasma unit to provide a platelet rich plasma unit having separated layers of platelet poor plasma and platelet concentrate; and e) isolating the separated layer of platelet concentrate to provide a platelet concentrate unit.

In some of the aforementioned methods, the method further comprises processing the isolated platelet concentrate unit to provide a platelet concentrate unit for pathogen inactivation.

In another aspect, the present disclosure provides a method of preparing a platelet product comprising: a) identifying a plurality of donated whole blood units according to one or more parameters selected from the group consisting of hematocrit, hemoglobin, donor gender, whole blood volume, packed cell volume and platelet count; b) selecting a subset of whole blood units from the plurality of donated whole blood units, wherein each unit of the selected subset is within one of at least two specified ranges for at least one of the one or more parameters; c) centrifuging the selected subset of units under the same centrifugation conditions to provide each unit having a separated layer of platelet rich plasma; and d) isolating the separated layer of platelet rich plasma to provide a platelet rich plasma unit. In some embodiments, the method comprises identifying the plurality of donated whole blood units according to two or more of the aforementioned parameters. In some embodiments, the method comprises identifying the plurality of donated whole blood units according to three or more said parameters. In some embodiments, the at least two specified ranges for a parameter are non-overlapping ranges. In some embodiments, the at least two specified ranges for a parameter are overlapping ranges (e.g., overlap by an end point of the ranges, overlap by about 1%, overlap by about 2%, overlap by about 3%). In some embodiments, each unit of the selected subset is substantially the same for the one or more parameters. In some embodiments, each unit of the selected subset differs by no more than about 5%, 10%, 15%, or 20% from each other for at least one of the one or more parameters. In some embodiments, the one or more parameters may further comprise donor age, whole blood storage time prior to processing (e.g., prior to initiating the method), blood bag size and/or donor history of platelet aggregation.

In some embodiments of the aforementioned methods, the one or more parameters include hematocrit. In some embodiments, the specified range for hematocrit in the selected subset of units is about 0.400 to about 0.480 L/L, about 0.400 to about 0.470 L/L, about 0.410 to about 0.480 L/L, about 0.380 L/L to about 0.435 L/L, about 0.435 L/L to about 0.500 L/L, about 0.440 L/L to about 0.500 L/L, about 0.380 L/L to about 0.420 L/L, about 0.420 L/L to about 0.460 L/L, about 0.425 L/L to about 0.460 L/L, about 0.460 L/L to about 0.500 L/L, or about 0.465 L/L to about 0.500 L/L. In some embodiments, the specified range for hematocrit in the selected subset of units is at least about 0.380 L/L and less than about 0.435 L/L, or at least about 0.435 L/L and less than about 0.500 L/L, or greater than about 0.435 L/L and less than about 0.500 L/L, or greater than about 0.435 L/L to about 0.500 L/L. In some embodiments, the specified range for hematocrit in the selected subset of units is at least about 0.380 L/L and less than about 0.435 L/L, or at least about 0.435 L/L and less than about 0.500 L/L. Hematocrit may also be represented as a percentage. In some embodiments, the specified range for hematocrit in the selected subset of units is about 40.0% to about 48.0%, about 40.0% to about 47.0%, about 41.0% to about 48.0%, about 38.0% to about 43.5%, about 43.5% to about 50.0%, about 44.0% to about 50.0%, about 38.0% to about 42.0%, about 42.0% to about 46.0%, about 42.5% to about 46.0%, about 46.0% to about 50.0%, or about 46.5% to about 50.0%. In some embodiments, the specified range for hematocrit in the selected subset of units is at least about 38.0% and less than about 43.5%, or at least about 43.5% and less than about 50.0%, or greater than about 43.5% and less than about 50.0%, or greater than about 43.5% to about 50.0%. In some embodiments, the one or more parameters include hemoglobin. In some embodiments, the specified range for hemoglobin in the selected subset of units is about 7.8-9.4 mmol/L, about 9.4-11.0 mmol/L, about 7.8-8.9 mmol, about 8.4-9.3 mmol, about 8.9-9.9 mmol/L, about 9.0-9.9 mmol, about 9.3-10.3 mmol, about 9.4-10.2 mmol, about 9.5-11.0 mmol/L, about 9.9-11.0 mmol/L, about 10.0-11.0 mmol. In some embodiments, the specified range for hemoglobin in the selected subset of units is about 13.5 g/dL to about 15.0 g/dL, about 15.1 g/dL to about 16.5 g/dL, or about 15.0 g/dL to about 16.5 g/dL. In some embodiments, the one or more parameters include donor gender. In some embodiments the specified range for donor gender in the selected subset of units is 100% female donors. In some embodiments, the specified range for donor gender in the selected subset of units is 100% male donors. In some embodiments, the specified range for donor gender is no more than one unit from a male donor together with the remaining units being from female donors. In some embodiments, the specified range for donor gender is no more than one unit from a female donor together with the remaining units being from male donors. In some embodiments, the one or more parameters include whole blood volume. In some embodiments, the specified range for whole blood volume in the selected subset of units is about 270-330 mL, about 315-385 mL, about 332-368 mL, about 360-440 mL, about 405-495 mL, about 405-490 mL, about 405-450 mL, about 405-435 mL, about 427-473 mL, about 430-480 mL, about 435-465 mL, about 450-550 mL, about 450-500 mL, about 450-495 mL, about 465-495 mL, or about 475-525 mL. In some embodiments, the one or more parameters include packed cell volume. In some embodiments, the specified range for packed cell volume (e.g., fraction packed cell volume) in the selected subset of units is about 0.40 to about 0.48, about 0.40 to about 0.47, about 0.41 to about 0.48, about 0.38 to about 0.44, about 0.44 to about 0.50, about 0.38 to about 0.42, about 0.42 to about 0.46, or about 0.46 to about 0.50. In some embodiments, the one or more parameters include platelet count. In some embodiments of the aforementioned methods, at least one of the one or more parameters is whole blood volume, and the at least two specified ranges include 405-450 mL and 451-495 mL. In some embodiments, at least one of the one or more parameters is whole blood volume, and the at least two specified ranges include 405-450 mL and 450-495 mL. In some embodiments, at least one of the one or more parameters is hematocrit, and the at least two specified ranges include about 0.380 L/L to about 0.435 L/L and about 0.440 L/L to about 0.500 L/L. In some embodiments, at least one of the one or more parameters is hematocrit, and the at least two specified ranges include about 0.380 L/L to about 0.435 L/L and about 0.435 L/L to about 0.500 L/L. In some embodiments, at least one of the one or more parameters is hemoglobin, and the at least two specified ranges include 7.8-9.4 mmol/L and 9.5-11.0 mmol/L. In some embodiments, at least one of the one or more parameters is hemoglobin, and the at least two specified ranges include 7.8-9.4 mmol/L and 9.4-11.0 mmol/L. In some embodiments, at least one of the one or more parameters is hemoglobin, and the at least two specified ranges include about 13.5 g/dL to about 15.0 g/dL and about 15.1 g/dL to about 16.5 g/dL. In some embodiments, at least one of the one or more parameters is hemoglobin, and the at least two specified ranges include about 13.5 g/dL to about 15.0 g/dL and about 15.0 g/dL to about 16.5 g/dL. In some embodiments, each unit of the selected subset of whole blood units is within the same specified range for two or more of the aforementioned parameters. In some embodiments, the two or more parameters include hematocrit and hemoglobin, hematocrit and donor gender, hematocrit and whole blood volume, hematocrit and packed cell volume or hematocrit and platelet count. In some embodiments, the two or more parameters include hemoglobin and donor gender, hemoglobin and whole blood volume, hemoglobin and packed cell volume or hemoglobin and platelet count. In some embodiments, the two or more parameters include donor gender and whole blood volume, donor gender and packed cell volume or donor gender and platelet count. In some embodiments, the two or more parameters include whole blood volume and packed cell volume or whole blood volume and platelet count. In some embodiments, the two or more parameters include packed cell volume and platelet count. In some embodiments, each unit of the selected subset of whole blood units is within the same specified range for three or more of the aforementioned parameters. In some embodiments, the three or more parameters include hematocrit, hemoglobin and donor gender. In some embodiments, the three or more parameters include hematocrit, hemoglobin and whole blood volume. In some embodiments, the three or more parameters include hematocrit, hemoglobin and packed cell volume. In some embodiments, the three or more parameters include hematocrit, hemoglobin and platelet count. In some embodiments, the three or more parameters include hematocrit, donor gender and whole blood volume. In some embodiments, the three or more parameters include hematocrit, donor gender and packed cell volume. In some embodiments, the three or more parameters include hematocrit, donor gender and platelet count. In some embodiments, the three or more parameters include hematocrit, whole blood volume and packed cell volume. In some embodiments, the three or more parameters include hematocrit, whole blood volume and platelet count. In some embodiments, the three or more parameters include hematocrit, packed cell volume and platelet count. In some embodiments, the three or more parameters include hemoglobin, donor gender and whole blood volume. In some embodiments, the three or more parameters include hemoglobin, donor gender and packed cell volume. In some embodiments, the three or more parameters include hemoglobin, donor gender and platelet count. In some embodiments, the three or more parameters include hemoglobin, whole blood volume and packed cell volume. In some embodiments, the three or more parameters include hemoglobin, whole blood volume and platelet count. In some embodiments, the three or more parameters include hemoglobin, packed cell volume and platelet count. In some embodiments, the three or more parameters include donor gender, whole blood volume and packed cell volume. In some embodiments, the three or more parameters include donor gender, whole blood volume and platelet count. In some embodiments, the three or more parameters include donor gender, packed cell volume and platelet count. In some embodiments, the three or more parameters include whole blood volume, packed cell volume and platelet count. In some embodiments, each unit of the selected subset of whole blood units is within the same specified range for four or more, or five or more of the aforementioned parameters. In some embodiments of the aforementioned methods, the specified range for each of the one or more parameters for the selected subset of whole blood units is narrower than the range for the same parameter in the plurality of donated whole blood units. In some embodiments of the aforementioned methods, the specified range for the parameter in the subset of whole blood units is narrower than the range for the same parameter for donated whole blood that meets the acceptance criteria of a regulatory agency or accrediting organization for donated whole blood. In some embodiments of the aforementioned methods, the regulatory agency is the U.S. Food and Drug Administration (FDA), the European Medicines Agency (EMA), the Australian Therapeutic Goods Administration (TGA), the China Food and Drug Administration (CFDA), or the Japan Ministry of Health, Labour, and Welfare (MHLW). In some embodiments of the aforementioned methods, the accrediting organization is the AABB or the European Directorate for the Quality of Medicines & HealthCare (EDQM).

In some embodiments of the aforementioned methods, the method further comprises selecting a first subset of whole blood units within a first specified range of the at least two specified ranges for a given parameter of the at least one or more parameters and selecting a second subset of whole blood units within a second specified range of the at least two specified ranges for the given parameter. In some embodiments of the aforementioned methods, the method further comprises centrifuging the first selected subset of whole blood units and the second selected subset of whole blood units under different centrifugation conditions. In some embodiments, the centrifugation conditions are determined by each of the at least two specified ranges for the at least one parameter. In some embodiments, the centrifugation conditions for each of the at least two specified ranges for the at least one parameter are different from each other. In some embodiments of the aforementioned methods, the specified range is one of at least three specified ranges for at least one of the one or more parameters. In some embodiments, at least one of the one or more parameters is whole blood volume, and the at least three specified ranges include 405-435 mL, 436-465 mL and 466-495 mL. In some embodiments, at least one of the one or more parameters is whole blood volume, and the at least three specified ranges include 405-435 mL, 435-465 mL and 465-495 mL. In some embodiments, at least one of the one or more parameters is hematocrit, and the at least three specified ranges include about 0.380 L/L to about 0.420 L/L, about 0.425 L/L to about 0.460 L/L, and about 0.465 L/L to about 0.500 L/L. In some embodiments, at least one of the one or more parameters is hematocrit, and the at least three specified ranges include about 0.380 L/L to about 0.420 L/L, about 0.420 L/L to about 0.460 L/L, and about 0.460 L/L to about 0.500 L/L. In some embodiments, at least one of the one or more parameters is hemoglobin, and the at least three specified ranges include 7.8-8.9 mmol/L, 9.0-9.9 mmol/L and 10.0-11.0 mmol/L. In some embodiments, at least one of the one or more parameters is hemoglobin, and the at least three specified ranges include 7.8-8.9 mmol/L, 8.9-9.9 mmol/L and 9.9-11.0 mmol/L. In some embodiments of the aforementioned methods, the specified range is one of at least four specified ranges for at least one of the one or more parameters. In some embodiments of the aforementioned methods, the isolated platelet rich plasma unit comprises less than about $5 \times 10^6$ red blood cells.

In some embodiments of the aforementioned methods, the method further comprises processing the isolated platelet rich plasma unit to provide a platelet rich plasma unit for pathogen inactivation. In some embodiments of the aforementioned methods, the method further comprises: e) centrifuging the isolated platelet rich plasma unit to provide a platelet rich plasma unit having separated layers of platelet poor plasma and platelet concentrate; and f) isolating the separated layer of platelet concentrate to provide a platelet concentrate unit. In some embodiments of the aforementioned methods, the method further comprises processing the isolated platelet concentrate unit to provide a platelet concentrate unit for pathogen inactivation.

In some embodiments of the aforementioned methods, the method comprises: a) identifying a plurality of donated whole blood units according to donor gender; b) selecting a first subset of whole blood units from the plurality of donated whole blood units, wherein each unit of the first selected subset is the same donor gender; c) centrifuging the first selected subset of units under the same centrifugation conditions to provide each unit having a separated layer of platelet rich plasma; d) isolating the separated layer of platelet rich plasma to provide a platelet rich plasma unit; e) centrifuging the isolated platelet rich plasma unit to provide a platelet rich plasma unit having separated layers of platelet poor plasma and platelet concentrate; f) isolating the separated layer of platelet concentrate to provide a platelet concentrate unit from the first subset of whole blood units; g) selecting a second subset of whole blood units from the plurality of donated whole blood units, wherein each unit of the second selected subset is the same donor gender, and wherein the donor gender of the second selected subset is different from the donor gender of the first selected subset; h) centrifuging the second selected subset of units under the same centrifugation conditions to provide each unit having a separated layer of platelet rich plasma, wherein the centrifugation conditions for the second subset of whole blood units are different from the centrifugation conditions of the first subset of whole blood units; i) isolating the separated layer of platelet rich plasma to provide a platelet rich plasma unit; j) centrifuging the isolated platelet rich plasma unit to provide a platelet rich plasma unit having separated layers of platelet poor plasma and platelet concentrate; and k) isolating the separated layer of platelet concentrate to provide a platelet concentrate unit from the second subset of whole blood units.

In some embodiments of the aforementioned methods, the isolated platelet concentrate unit comprises about $0.1 \times 10^{11}$ to about $2.2 \times 10^{11}$ platelets. In some embodiments, the isolated platelet concentrate unit comprises about $0.4 \times 10^{11}$ to about $1.1 \times 10^{11}$ platelets. In some embodiments, the isolated platelet concentrate unit comprises about $0.4 \times 10^{11}$ to about $0.8 \times 10^{11}$ platelets. In some embodiments, the isolated platelet concentrate unit comprises about $0.6 \times 10^{11}$ to about $0.8 \times 10^{11}$ platelets. In some embodiments, the isolated platelet concentrate unit comprises about $0.8 \times 10^{11}$ to about $1.1 \times 10^{11}$ platelets. In some embodiments, the isolated platelet concentrate unit comprises about $0.8 \times 10^{11}$ platelets. In some embodiments, the isolated platelet concentrate unit comprises about $0.9 \times 10^{11}$ platelets. In some embodiments, the isolated platelet concentrate unit comprises about $1.0 \times 10^{11}$ platelets. In some embodiments, the isolated platelet concentrate unit comprises about $1.1 \times 10^{11}$ platelets.

In some embodiments of the aforementioned methods, the isolated platelet concentrate further comprises donor plasma. In some embodiments, the donor plasma is an amount of remaining plasma from the platelet rich plasma unit. In some embodiments, the donor plasma is plasma from the same donor as the isolated platelet concentrate. In some embodiments, the donor plasma is plasma from a different donor than the donor of the isolated platelet concentrate. In some embodiments, the donor plasma is fresh frozen plasma.

In some embodiments of the aforementioned methods, the isolated platelet concentrate has a volume of about 45-80 mL. In some embodiments, the isolated platelet concentrate has a volume of about 50-75 mL. In some embodiments, the isolated platelet concentrate has a volume of about 45-55 mL. In some embodiments, the isolated platelet concentrate has a volume of about 50-80 mL, about 50-70 mL, about 50-65 mL, about 50-60 mL about 50-55 mL, about 45-50 mL, about 45-55 mL, about 45-60 mL, about 45-65 mL, about 45-70 mL, about 45-75 mL, about 55-60 mL, about 55-65 mL, about 55-70 mL, about 55-75 mL, about 55-80 mL, about 60-65 mL, about 60-70 mL, about 60-75 mL, about 60-80 mL, about 65-70 mL, about 65-75 mL, about 65-80 mL, about 70-75 mL, about 70-80 mL, or about 75-80 mL. In some embodiments of the aforementioned methods, the isolated platelet concentrate has a volume of about 15-45 mL. In some embodiments, the isolated platelet concentrate has a volume of about 15-25 mL. In some embodiments, the isolated platelet concentrate has a volume of about 25-35 mL. In some embodiments, the isolated platelet concentrate has a volume of about 15-20 mL, about 15-30 mL, about 15-35 mL, about 15-40 mL, about 20-25 mL, about 20-30 mL, about 20-35 mL, about 20-40 mL, about 20-45 mL, about 25-30 mL, about 25-40 mL, about 25-45 mL, about 30-35 mL, about 30-40 mL, about 30-45 mL, about 35-40 mL, about 35-45 mL or about 40-45 mL. In some embodiments of the aforementioned methods, the isolated platelet concentrate has a volume of less than about 5 mL.

In some of the aforementioned methods, the method further comprises processing the isolated platelet concentrate unit to provide a platelet concentrate unit for pathogen inactivation and/or storage. In some embodiments of the aforementioned methods, the isolated platelet concentrate unit is further processed by addition of an additive solution (e.g., platelet additive solution, PAS) to provide a PAS platelet concentrate unit (e.g. a PAS platelet concentrate unit for pathogen inactivation and/or storage). In some embodiments of the aforementioned methods, the method further comprises adding an additive solution (e.g., platelet additive solution, PAS) to the isolated platelet concentrate to provide a PAS platelet concentrate unit (e.g. for pathogen inactivation and/or storage). In some embodiments of the aforementioned methods, the isolated platelet concentrate is a PAS platelet concentrate unit (e.g. for pathogen and/or storage) that further comprises an additive solution (e.g., platelet additive solution, PAS). In some embodiments, the PAS platelet concentrate unit comprises about 5 to 50% plasma and about 95 to 50% additive solution. In some embodiments, the PAS platelet concentrate unit comprises about 30-50% plasma. In some embodiments, the PAS platelet concentrate unit comprises about 5-10%, about 5-15%, about 51-20%, about 5-25%, about 5-30%, about 5-35%, about 5-40%, about 5-45%, about 10-15%, about 10-20%, about 10-25%, about 10-30%, about 10-35%, about 10-40%, about 10-45%, about 10-50%, about 15-20%, about 15-25%, about 15-30%, about 15-35%, about 15-40%, about 15-45%, about 15-50%, about 20-25%, about 20-30%, about 20-35%, about 20-40%, about 20-45%, about 20-50%, about 25-30%, about 25-35%, about 25-40%, about 25-45%, about 25-50%, about 30-35%, about 30-40%, about 30-45%, about 35-40%, about 35-45%, about 35-50%, about 40-45%, about 40-50% or about 45-50% plasma. In some embodiments, the PAS platelet concentrate unit comprises greater than 95% additive solution. In some embodiments, the PAS platelet concentrate unit comprises greater than 50%, 55%, 60%, 65%, 70%, 75%, 80%, 85% or 90% additive solution. In some embodiments, the additive solution is a platelet additive solution.

In some embodiments of the aforementioned methods, the method further comprises storing the isolated platelet concentrate unit for a period of about 2 hours to about 7 days. In some embodiments of the aforementioned methods, the method further comprises storing the isolated platelet concentrate unit for a period of about 2 hours to about 5 days. In some embodiments, the isolated platelet concentrate is stored for about 2 hours. In some embodiments, the isolated platelet concentrate is stored for about 1 hour, about 3 hours, about 4 hours, about 5 hours, about 6 hours, about 7 hours, about 8 hours, about 10 hours, about 12 hours, about 14 hours, about 16 hours, about 18 hours, about 20 hours, about 22 hours or about 24 hours. In some embodiments, the isolated platelet concentrate is stored for about 1 day. In some embodiments, the isolated platelet concentrate is stored for about 2 days, about 3 days, about 4 days or about 5 days. In some embodiments, the isolated platelet concentrate is stored for about 6 days or about 7 days. In some embodiments, the isolated platelet concentrate is stored with agitation. In some embodiments, the isolated platelet concentrate unit is stored for an initial period without agitation and subsequent period with agitation.

In some embodiments of the aforementioned methods, the method further comprises pooling two or more of the isolated platelet concentrate units into one container to provide a pooled platelet product. In some embodiments, the method comprises pooling 3-6 isolated platelet concentrate units. In some embodiments, the method comprises pooling 7-10 isolated platelet concentrate units. In some embodiments, the method comprises pooling 5-8 isolated platelet concentrate units. In some embodiments, the pooled platelet concentrates (e.g., pooled platelet product) comprises about $1.0 \times 10^{11}$ to about $8 \times 10^{11}$ platelets. In some embodiments, the pooled platelet product comprises about $2.0 \times 10^{11}$ to about $7.0 \times 10^{11}$ platelets. In some embodiments, the pooled platelet product comprises about $2.5 \times 10^{11}$ to about $4.0 \times 10^{11}$ platelets. In some embodiments, the pooled platelet product comprises about $4.0 \times 10^{11}$ to about $6.4 \times 10^{11}$ platelets. In some embodiments, the pooled platelet product comprises about $4.0 \times 10^{11}$ to about $7.0 \times 10^{11}$ platelets. In some embodiments, the pooled platelet product comprises about $6.0 \times 10^{11}$ to about $7.0 \times 10^{11}$ platelets. In some embodiments, the pooled platelet product has a platelet concentration of about $0.5 \times 10^9$/mL to about $2.0 \times 10^9$/mL. In some embodiments, the pooled platelet product has a platelet concentration of about $0.7 \times 10^9$/mL to about $1.7 \times 10^9$/mL. In some embodiments, the pooled platelet product has a platelet concentration of about $0.7 \times 10^9$/mL to about $1.5 \times 10^9$/mL. In some embodiments, the two or more pooled platelet concentrate units are ABO blood group matched. In some embodiments, the two or more pooled platelet concentrate units are from the same selected subset of units. In some embodiments, the two or more pooled platelet concentrate units are from more than one selected subset of units.

In some embodiments of the aforementioned methods, the donated whole blood units comprise an anticoagulant. In some embodiments, the anticoagulant is CPD or CP2D.

In some embodiments of the aforementioned methods, the whole blood donation time is less than about 15 minutes, or less than about 12 minutes, or less than about 10 minutes. In some embodiments of the aforementioned methods, the method is performed immediately after whole blood collection. In some embodiments of the aforementioned methods, the whole blood unit is stored for a period of time prior to processing. In some embodiments of the aforementioned methods, the whole blood unit is stored for a period of time prior to initiating the method. In some embodiments, the whole blood unit is stored for at least 1 hour, at least 2 hr, at least 3 hr, at least 4 hr, at least 5 hr, at least 6 hr, at least 7 hr, at least 8 hr or more, or overnight. In some embodiments, the whole blood unit is stored for less than 24 hours. In some embodiments, the whole blood unit is stored for less than 8 hours. In some embodiments, the whole blood unit is stored for at least 8 hr and less than 24 hr. In some embodiments, the whole blood unit is stored at room temperature.

In some embodiments of the aforementioned methods, the method is performed (e.g., initiated) at least 1 hour, at least 2 hours, at least 3 hours, at least 4 hours, at least 5 hours, at least 6 hours, at least 7 hours, at least 8 hours or more after collection of the donated whole blood units. In some embodiments, the method is performed less than 24 hours after collection of the donated whole blood units. In some embodiments, the method is performed less than 8 hours after collection of the donated whole blood units. In some embodiments, the method is performed more than 8 hours and less than 24 hours after collection of the donated whole blood units. In some embodiments, the method is performed after an overnight storage of the donated whole blood units.

In some embodiments of the aforementioned methods, the donated whole blood units are cooled from their initial post-collection temperature. In some embodiments, the whole blood units are cooled to room temperature following donation. In some embodiments, the whole blood units are cooled to 18-25° C. following donation. In some embodiments, the whole blood units are cooled to 20-24° C. following donation.

In some embodiments of the aforementioned methods, the method further comprises treating with a pathogen inactivation compound to inactivate pathogens, if present. In some embodiments, the pathogen inactivation compound is a photoactive pathogen inactivation compound selected from the group consisting of a psoralen, an isoalloxazine, an alloxazine, a phthalocyanine, a phenothiazine, a porphyrin, and merocyanine 540. In some embodiments, the pathogen inactivation compound is a psoralen. In some embodiments, the pathogen inactivation compound is amotosalen.

In another aspect, the present disclosure provides a method of preparing a pooled platelet product, comprising: a) identifying a plurality of donated whole blood units according to one or more parameters selected from the group consisting of hematocrit, hemoglobin and donor gender; b) selecting a subset of whole blood units from the plurality of donated whole blood units, wherein each unit of the selected subset is within one of at least two specified ranges for at least one of the one or more parameters; c) centrifuging the selected subset of units under the same centrifugation conditions to provide each unit having a separated layer of platelet rich plasma; d) isolating the separated layer of platelet rich plasma to provide a platelet rich plasma unit; e) centrifuging the isolated platelet rich plasma unit to provide a platelet rich plasma unit having separated layers of platelet poor plasma and platelet concentrate; f) isolating the separated layer of platelet concentrate to provide a platelet concentrate unit; and g) pooling at least seven isolated platelet concentrate units into one container to provide a pooled platelet product. In some embodiments, seven or eight isolated platelet concentrates units are pooled to provide a pooled platelet product. In some embodiments, the method further comprises treating the pooled platelet product with a pathogen inactivation compound to inactivate pathogens, if present. In some embodiments, the method further comprises transferring the pooled platelet product into two storage containers to provide a double dose platelet product. In some embodiments, the method comprises identifying the plurality of donated whole blood units according to two of the said parameters. In some embodiments, the method comprises identifying the plurality of donated whole blood units according to all three of the said parameters.

In some embodiments of the aforementioned methods, the at least two specified ranges for a parameter are non-overlapping ranges. In some embodiments, the at least two specified ranges for a parameter are overlapping ranges (e.g., overlap by an end point of the ranges, overlap by about 1%, overlap by about 2%, overlap by about 3%). In some embodiments, each unit of the selected subset is substantially the same for the one or more parameters. In some embodiments, each unit of the selected subset differs by no more than about 5%, 10%, 15%, or 20% from each other for at least one of the one or more parameters. In some embodiments, each unit of the selected subset of whole blood units is within the same specified range for two or more of said parameters.

In some embodiments of the aforementioned methods, the one or more parameters include hematocrit. In some embodiments, the specified range for hematocrit in the selected subset of units is about 0.400 to about 0.480 L/L, about 0.400 to about 0.470 L/L, about 0.410 to about 0.480 L/L, about 0.380 L/L to about 0.435 L/L, about 0.435 L/L to about 0.500 L/L, about 0.440 L/L to about 0.500 L/L, about 0.380 L/L to about 0.420 L/L, about 0.420 L/L to about 0.460 L/L, about 0.425 L/L to about 0.460 L/L, about 0.460 L/L to about 0.500 L/L, or about 0.465 L/L to about 0.500 L/L. In some embodiments, the specified range for hematocrit in the selected subset of units is at least about 0.380 L/L and less than about 0.435 L/L, or at least about 0.435 L/L and less than about 0.500 L/L, or greater than about 0.435 L/L and less than about 0.500 L/L, or greater than about 0.435 L/L to about 0.500 L/L. In some embodiments, the specified range for hematocrit in the selected subset of units is at least about 0.380 L/L and less than about 0.435 L/L, or at least about 0.435 L/L and less than about 0.500 L/L. Hematocrit may also be represented as a percentage. In some embodiments, the specified range for hematocrit in the selected subset of units is about 40.0% to about 48.0%, about 40.0% to about 47.0%, about 41.0% to about 48.0%, about 38.0% to about 43.5%, about 43.5% to about 50.0%, about 44.0% to about 50.0%, about 38.0% to about 42.0%, about 42.0% to about 46.0%, about 42.5% to about 46.0%, about 46.0% to about 50.0%, or about 46.5% to about 50.0%. In some embodiments, the specified range for hematocrit in the selected subset of units is at least about 38.0% and less than about 43.5%, or at least about 43.5% and less than about 50.0%, or greater than about 43.5% and less than about 50.0%, or greater than about 43.5% to about 50.0%. In some embodiments, the one or more parameters include hemoglobin. In some embodiments, the specified range for hemoglobin in the selected subset of units is about 7.8-9.4 mmol/L, about 9.4-11.0 mmol/L, about 7.8-8.9 mmol, about 8.4-9.3 mmol, about 8.9-9.9 mmol/L, about 9.0-9.9 mmol, about 9.3-10.3 mmol, about 9.4-10.2 mmol, about 9.5-11.0 mmol/L, about 9.9-11.0 mmol/L, or about 10.0-11.0 mmol. In some embodiments, the specified range for hemoglobin in the selected subset of units is about 13.5 g/dL to about 15.0 g/dL, about 15.1 g/dL to about 16.5 g/dL, or about 15.0 g/dL to about 16.5 g/dL. In some embodiments, the one or more parameters include donor gender. In some embodiments the specified range for donor gender in the selected subset of units is 100% female donors. In some embodiments, the specified range for donor gender in the selected subset of units is 100% male donors. In some embodiments, the specified range for donor gender is no more than one unit from a male donor together with the remaining units being from female donors. In some embodiments, the specified range for donor gender is no more than one unit from a female donor together with the remaining units being from male donors.

In some embodiments, at least one of the one or more parameters is hematocrit, and the at least two specified ranges include about 0.380 L/L to about 0.435 L/L and about 0.440 L/L to about 0.500 L/L. In some embodiments, at least one of the one or more parameters is hematocrit, and the at least two specified ranges include about 0.380 L/L to about 0.435 L/L and about 0.435 L/L to about 0.500 L/L. In some embodiments, at least one of the one or more parameters is hemoglobin, and the at least two specified ranges include 7.8-9.4 mmol/L and 9.5-11.0 mmol/L. In some embodiments, at least one of the one or more parameters is hemoglobin, and the at least two specified ranges include 7.8-9.4 mmol/L and 9.4-11.0 mmol/L. In some embodiments, at least one of the one or more parameters is hemoglobin, and the at least two specified ranges include about 13.5 g/dL to about 15.0 g/dL and about 15.1 g/dL to about 16.5 g/dL. In some embodiments, at least one of the one or more parameters is hemoglobin, and the at least two specified ranges include about 13.5 g/dL to about 15.0 g/dL and about 15.0 g/dL to about 16.5 g/dL. In some embodiments, each unit of the selected subset of whole blood units is within the same specified range for two or more of the aforementioned parameters.

In some embodiments of the aforementioned methods, the specified range for each of the one or more parameters for the selected subset of whole blood units is narrower than the range for the same parameter in the plurality of donated whole blood units. In some embodiments of the aforementioned methods, the specified range for the parameter in the subset of whole blood units is narrower than the range for the same parameter for donated whole blood that meets the acceptance criteria of a regulatory agency or accrediting organization for donated whole blood. In some of the aforementioned methods, the regulatory agency is the U.S. Food and Drug Administration (FDA), the European Medicines Agency (EMA), the Australian Therapeutic Goods Administration (TGA), the China Food and Drug Administration (CFDA), or the Japan Ministry of Health, Labour, and Welfare (MHLW). In some of the aforementioned methods, the accrediting organization is the AABB or the European Directorate for the Quality of Medicines & HealthCare (EDQM).

In some embodiments of the aforementioned methods, the method further comprises selecting a first subset of whole blood units within a first specified range of the at least two specified ranges for a given parameter of the at least one or more parameters and selecting a second subset of whole blood units within a second specified range of the at least two specified ranges for the given parameter. In some embodiments of the aforementioned methods, the method further comprises centrifuging the first selected subset of whole blood units and the second selected subset of whole blood units under different centrifugation conditions. In some embodiments, the centrifugation conditions are determined by each of the at least two specified ranges for the at least one parameter. In some embodiments, the centrifugation conditions for each of the at least two specified ranges for the at least one parameter are different from each other. In some embodiments of the aforementioned methods, the specified range is one of at least three specified ranges for at least one of the one or more parameters. In some embodiments, at least one of the one or more parameters is hematocrit, and the at least three specified ranges include about 0.380 L/L to about 0.420 L/L, about 0.425 L/L to about 0.460 L/L, and about 0.465 L/L to about 0.500 L/L. In some embodiments, at least one of the one or more parameters is hematocrit, and the at least three specified ranges include about 0.380 L/L to about 0.420 L/L, about 0.420 L/L to about 0.460 L/L, and about 0.460 L/L to about 0.500 L/L. In some embodiments, at least one of the one or more parameters is hemoglobin, and the at least three specified ranges include 7.8-8.9 mmol/L, 9.0-9.9 mmol/L and 10.0-11.0 mmol/L. In some embodiments, at least one of the one or more parameters is hemoglobin, and the at least three specified ranges include 7.8-8.9 mmol/L, 8.9-9.9 mmol/L and 9.9-11.0 mmol/L. In some embodiments of the aforementioned methods, the specified range is one of at least four specified ranges for at least one of the one or more parameters. In some embodiments of the aforementioned methods, the isolated platelet rich plasma unit comprises less than about $5 \times 10^6$ red blood cells. In some embodiments of the aforementioned methods, the method further comprises processing the isolated platelet concentrate unit to provide a platelet concentrate unit for pathogen inactivation.

In some embodiments of the aforementioned methods, the isolated platelet concentrate unit comprises about $0.1 \times 10^{11}$ to about $2.2 \times 10^{11}$ platelets. In some embodiments, the isolated platelet concentrate unit comprises about $0.4 \times 10^{11}$ to about $1.1 \times 10^{11}$ platelets. In some embodiments, the isolated platelet concentrate unit comprises about $0.4 \times 10^{11}$ to about $0.8 \times 10^{11}$ platelets. In some embodiments, the isolated platelet concentrate unit comprises about $0.6 \times 10^{11}$ to about $0.8 \times 10^{11}$ platelets. In some embodiments, the isolated platelet concentrate unit comprises about $0.8 \times 10^{11}$ to about $1.1 \times 10^{11}$ platelets. In some embodiments, the isolated platelet concentrate unit comprises about $0.8 \times 10^{11}$ platelets. In some embodiments, the isolated platelet concentrate unit comprises about $0.9 \times 10^{11}$ platelets. In some embodiments, the isolated platelet concentrate unit comprises about $1.0 \times 10^{11}$ platelets. In some embodiments, the isolated platelet concentrate unit comprises about $1.1 \times 10^{11}$ platelets.

In some embodiments of the aforementioned methods, the isolated platelet concentrate further comprises donor plasma. In some embodiments, the donor plasma is an amount of remaining plasma from the platelet rich plasma unit. In some embodiments, the donor plasma is plasma from the same donor as the isolated platelet concentrate. In some embodiments, the donor plasma is plasma from a different donor than the donor of the isolated platelet concentrate. In some embodiments, the donor plasma is fresh frozen plasma.

In some embodiments of the aforementioned methods, the isolated platelet concentrate has a volume of about 45-80 mL. In some embodiments, the isolated platelet concentrate has a volume of about 50-75 mL. In some embodiments, the isolated platelet concentrate has a volume of about 45-55 mL. In some embodiments, the isolated platelet concentrate has a volume of about 50-80 mL, about 50-70 mL, about 50-65 mL, about 50-60 mL about 50-55 mL, about 45-50 mL, about 45-55 mL, about 45-60 mL, about 45-65 mL, about 45-70 mL, about 45-75 mL, about 55-60 mL, about 55-65 mL, about 55-70 mL, about 55-75 mL, about 55-80 mL, about 60-65 mL, about 60-70 mL, about 60-75 mL, about 60-80 mL, about 65-70 mL, about 65-75 mL, about 65-80 mL, about 70-75 mL, about 70-80 mL, or about 75-80 mL. In some embodiments of the aforementioned methods, the isolated platelet concentrate has a volume of about 15-45 mL. In some embodiments, the isolated platelet concentrate has a volume of about 15-25 mL. In some embodiments, the isolated platelet concentrate has a volume of about 25-35 mL. In some embodiments, the isolated platelet concentrate has a volume of about 15-20 mL, about 15-30 mL, about 15-35 mL, about 15-40 mL, about 20-25 mL, about 20-30 mL, about 20-35 mL, about 20-40 mL, about 20-45 mL, about 25-30 mL, about 25-40 mL, about 25-45 mL, about 30-35 mL, about 30-40 mL, about 30-45 mL, about 35-40 mL, about 35-45 mL or about 40-45 mL. In some embodiments of the aforementioned methods, the isolated platelet concentrate has a volume of less than about 5 mL.

In some of the aforementioned methods, the method further comprises processing the isolated platelet concentrate unit to provide a platelet concentrate unit for pathogen inactivation and/or storage. In some embodiments of the aforementioned methods, the isolated platelet concentrate unit is further processed by addition of an additive solution (e.g., platelet additive solution, PAS) to provide a PAS platelet concentrate unit (e.g. a PAS platelet concentrate unit for pathogen inactivation and/or storage). In some embodiments of the aforementioned methods, the method further comprises adding an additive solution (e.g., platelet additive solution, PAS) to the isolated platelet concentrate to provide a PAS platelet concentrate unit (e.g. for pathogen inactivation and/or storage). In some embodiments of the aforementioned methods, the isolated platelet concentrate is a PAS platelet concentrate unit (e.g. for pathogen and/or storage) that further comprises an additive solution (e.g., platelet additive solution, PAS). In some embodiments, the PAS platelet concentrate unit comprises about 5 to 50% plasma and about 95 to 50% additive solution. In some embodiments, the PAS platelet concentrate unit comprises about 30-50% plasma. In some embodiments, the PAS platelet concentrate unit comprises about 5-10%, about 5-15%, about 51-20%, about 5-25%, about 5-30%, about 5-35%, about 5-40%, about 5-45%, about 10-15%, about 10-20%, about 10-25%, about 10-30%, about 10-35%, about 10-40%, about 10-45%, about 10-50%, about 15-20%, about 15-25%, about 15-30%, about 15-35%, about 15-40%, about 15-45%, about 15-50%, about 20-25%, about 20-30%, about 20-35%, about 20-40%, about 20-45%, about 20-50%, about 25-30%, about 25-35%, about 25-40%, about 25-45%, about 25-50%, about 30-35%, about 30-40%, about 30-45%, about 35-40%, about 35-45%, about 35-50%, about 40-45%, about 40-50% or about 45-50% plasma. In some embodiments, the PAS platelet concentrate unit comprises greater than 95% additive solution. In some embodiments, the PAS platelet concentrate unit comprises greater than 50%, 55%, 60%, 65%, 70%, 75%, 80%, 85% or 90% additive solution. In some embodiments, the additive solution is a platelet additive solution.

In some embodiments of the aforementioned methods, the method further comprises storing the isolated platelet concentrate unit for a period of about 2 hours to about 7 days. In some embodiments of the aforementioned methods, the method further comprises storing the isolated platelet concentrate unit for a period of about 2 hours to about 5 days. In some embodiments, the isolated platelet concentrate is stored for about 2 hours. In some embodiments, the isolated platelet concentrate is stored for about 1 hour, about 3 hours, about 4 hours, about 5 hours, about 6 hours, about 7 hours, about 8 hours, about 10 hours, about 12 hours, about 14 hours, about 16 hours, about 18 hours, about 20 hours, about 22 hours or about 24 hours. In some embodiments, the isolated platelet concentrate is stored for about 1 day. In some embodiments, the isolated platelet concentrate is stored for about 2 days, about 3 days, about 4 days or about 5 days. In some embodiments, the isolated platelet concentrate is stored for about 1 day. In some embodiments, the isolated platelet concentrate is stored for about 6 days or about 7 days. In some embodiments, the isolated platelet concentrate is stored with agitation. In some embodiments, the isolated platelet concentrate unit is stored for an initial period without agitation and subsequent period with agitation.

In some embodiments of the aforementioned methods, the method comprises pooling 7-12 isolated platelet concentrate units (e.g., to prepare a pooled platelet product). In some embodiments of the aforementioned methods, the method comprises pooling 7 or 8 isolated platelet concentrate units. In some embodiments of the aforementioned methods, the method comprises pooling 7 isolated platelet concentrate units. In some embodiments of the aforementioned methods, the method comprises pooling 8 isolated platelet concentrate units. In some embodiments, the pooled platelet product comprises about $1.0 \times 10^{11}$ to about $8 \times 10^{11}$ platelets. In some embodiments, the pooled platelet product comprises about $2.0 \times 10^{11}$ to about $7.0 \times 10^{11}$ platelets. In some embodiments, the pooled platelet product comprises about $2.5 \times 10^{11}$ to about $4.0 \times 10^{11}$ platelets. In some embodiments, the pooled platelet product comprises about $4.0 \times 10^{11}$ to about $6.4 \times 10^{11}$ platelets. In some embodiments, the pooled platelet product comprises about $4.0 \times 10^{11}$ to about $7.0 \times 10^{11}$ platelets. In some embodiments, the pooled platelet product comprises about $6.0 \times 10^{11}$ to about $7.0 \times 10^{11}$ platelets. In some embodiments, the pooled platelet product has a platelet concentration of about $0.5 \times 10^{9}$/mL to about $2.0 \times 10^{9}$/mL. In some embodiments, the pooled platelet product has a platelet concentration of about $0.7 \times 10^{9}$/mL to about $1.7 \times 10^{9}$/mL. In some embodiments, the pooled platelet product has a platelet concentration of about $0.7 \times 10^{9}$/mL to about $1.5 \times 10^{9}$/mL. In some embodiments, the pooled platelet product comprises at least about $6.0 \times 10^{11}$ platelets. In some embodiments, the pooled platelet concentrate units are ABO blood group matched. In some embodiments, the pooled platelet concentrate units are from the same selected subset of units. In some embodiments, the pooled platelet concentrate units are from more than one selected subset of units. In some embodiments, the at least seven isolated platelet concentrate units are from the same selected subset. In some embodiments, the at least seven isolated platelet concentrate units are from different selected subsets. In some embodiments, the at least seven isolated platelet concentrate units are from at least two, at least three, at least four or more different selected subsets. In some embodiments, the double dose platelet product comprises at least about $1 \times 10^{11}$, at least about $2 \times 10^{11}$, or at least about $3 \times 10^{11}$ platelets per storage container.

In some embodiments of the aforementioned methods, the whole blood donation time is less than about 15 minutes, or less than about 12 minutes, or less than about 10 minutes. In some embodiments of the aforementioned methods, the method is performed immediately after whole blood collection. In some embodiments of the aforementioned methods, the whole blood unit is stored for a period of time prior to processing. In some embodiments of the aforementioned methods, the whole blood unit is stored for a period of time prior to initiating the method. In some embodiments, the whole blood unit is stored for at least 1 hour, at least 2 hr, at least 3 hr, at least 4 hr, at least 5 hr, at least 6 hr, at least 7 hr, at least 8 hr or more, or overnight. In some embodiments, the whole blood unit is stored for less than 24 hours. In some embodiments, the whole blood unit is stored for less than 8 hours. In some embodiments, the whole blood unit is stored for at least 8 hr and less than 24 hr. In some embodiments, the whole blood unit is stored at room temperature. In some embodiments of the aforementioned methods, the donated whole blood units comprise an anticoagulant. In some embodiments, the anticoagulant is CPD or CP2D.

In some embodiments of the aforementioned methods, the method is performed (e.g., initiated) at least 1 hour, at least 2 hours, at least 3 hours, at least 4 hours, at least 5 hours, at least 6 hours, at least 7 hours, at least 8 hours or more after collection of the donated whole blood units. In some embodiments, the method is performed less than 24 hours after collection of the donated whole blood units. In some embodiments, the method is performed less than 8 hours after collection of the donated whole blood units. In some embodiments, the method is performed more than 8 hours and less than 24 hours after collection of the donated whole blood units. In some embodiments, the method is performed after an overnight storage of the donated whole blood units.

In some embodiments of the aforementioned methods, the donated whole blood units are cooled from their initial post-collection temperature. In some embodiments, the whole blood units are cooled to room temperature following donation. In some embodiments, the whole blood units are cooled to 18-25° C. following donation. In some embodiments, the whole blood units are cooled to 20-24° C. following donation.

In some embodiments of the aforementioned methods, the method further comprises treating with a pathogen inactivation compound to inactivate pathogens, if present. In some embodiments, the pathogen inactivation compound is a photoactive pathogen inactivation compound selected from the group consisting of a psoralen, an isoalloxazine, an alloxazine, a phthalocyanine, a phenothiazine, a porphyrin, and merocyanine 540. In some embodiments, the pathogen inactivation compound is a psoralen. In some embodiments, the pathogen inactivation compound is amotosalen. In some embodiments of the aforementioned methods, the method further comprises a leukoreduction step. In some embodiments, the leukoreduction step is a filtration step.

In another aspect, the present disclosure provides a method of preparing a pooled platelet product, comprising: a) selecting a subset of whole blood units from a plurality of donated whole blood units; b) centrifuging the selected subset of units under the same centrifugation conditions to provide each unit having a separated layer of platelet rich plasma; c) isolating the separated layer of platelet rich plasma to provide a platelet rich plasma unit; d) centrifuging the isolated platelet rich plasma unit to provide a platelet rich plasma unit having separated layers of platelet poor plasma and platelet concentrate; e) isolating the separated layer of platelet concentrate to provide a platelet concentrate unit from the subset of whole blood units; f) pooling at least seven (e.g., seven, eight) isolated platelet concentrate units into one container to provide a pooled platelet product (e.g., said pooled platelet product comprising at least about $6.0 \times 10^{11}$ platelets); g) treating the pooled platelet product with a pathogen inactivation compound to inactivate pathogens, if present; and h) transferring the pooled platelet product into two storage containers to provide a double dose platelet product (e.g., said double dose platelet product each comprising at least about $1 \times 10^{11}$, at least about $2 \times 10^{11}$, or at least about $3 \times 10^{11}$ platelets per storage container).

In another aspect, the present disclosure provides a method of preparing a pooled platelet product, comprising: a) identifying a plurality of donated whole blood units according to donor gender; b) selecting a first subset of whole blood units from the plurality of donated whole blood units, wherein each unit of the first selected subset is the same donor gender; c) centrifuging the first selected subset of units under the same centrifugation conditions to provide each unit having a separated layer of platelet rich plasma; d) isolating the separated layer of platelet rich plasma to provide a platelet rich plasma unit; e) centrifuging the isolated platelet rich plasma unit to provide a platelet rich plasma unit having separated layers of platelet poor plasma and platelet concentrate; f) isolating the separated layer of platelet concentrate to provide a platelet concentrate unit from the first subset of whole blood units; g) selecting a second subset of whole blood units from the plurality of donated whole blood units, wherein each unit of the second selected subset is the same donor gender, and wherein the donor gender of the second selected subset is different from the donor gender of the first selected subset; h) centrifuging the second selected subset of units under the same centrifugation conditions to provide each unit having a separated layer of platelet rich plasma, wherein the centrifugation conditions for the second subset of whole blood units are different from the centrifugation conditions of the first subset of whole blood units; i) isolating the separated layer of platelet rich plasma to provide a platelet rich plasma unit; j) centrifuging the isolated platelet rich plasma unit to provide a platelet rich plasma unit having separated layers of platelet poor plasma and platelet concentrate; k) isolating the separated layer of platelet concentrate to provide a platelet concentrate unit from the second subset of whole blood units; and l) pooling at least seven isolated platelet concentrate units into one container to provide a pooled platelet product. In some embodiments, seven or eight isolated platelet concentrates units are pooled to provide a pooled platelet product. In some embodiments, the method further comprises treating the pooled platelet product with a pathogen inactivation compound to inactivate pathogens, if present. In some embodiments, the method further comprises transferring the pooled platelet product into two storage containers to provide a double dose platelet product.

In some embodiments of the aforementioned methods, the isolated platelet concentrate unit comprises about $0.1 \times 10^{11}$ to about $2.2 \times 10^{11}$ platelets. In some embodiments, the isolated platelet concentrate unit comprises about $0.4 \times 10^{11}$ to about $1.1 \times 10^{11}$ platelets. In some embodiments, the isolated platelet concentrate unit comprises about $0.4 \times 10^{11}$ to about $0.8 \times 10^{11}$ platelets. In some embodiments, the isolated platelet concentrate unit comprises about $0.6 \times 10^{11}$ to about $0.8 \times 10^{11}$ platelets. In some embodiments, the isolated platelet concentrate unit comprises about $0.8 \times 10^{11}$ to about $1.1 \times 10^{11}$ platelets. In some embodiments, the isolated platelet concentrate unit comprises about $0.8 \times 10^{11}$ platelets. In some embodiments, the isolated platelet concentrate unit comprises about $0.9 \times 10^{11}$ platelets. In some embodiments, the isolated platelet concentrate unit comprises about $1.0 \times 10^{11}$ platelets. In some embodiments, the isolated platelet concentrate unit comprises about $1.1 \times 10^{11}$ platelets. In some embodiments of the aforementioned methods, the isolated platelet rich plasma unit comprises less than about $5 \times 10^6$ red blood cells. In some embodiments of the aforementioned methods, the method further comprises processing the isolated platelet concentrate unit to provide a platelet concentrate unit for pathogen inactivation.

In some embodiments of the aforementioned methods, the isolated platelet concentrate further comprises donor plasma. In some embodiments, the donor plasma is an amount of remaining plasma from the platelet rich plasma unit. In some embodiments, the donor plasma is plasma from the same donor as the isolated platelet concentrate. In some embodiments, the donor plasma is plasma from a different donor than the donor of the isolated platelet concentrate. In some embodiments, the donor plasma is fresh frozen plasma.

In some embodiments of the aforementioned methods, the isolated platelet concentrate has a volume of about 45-80 mL. In some embodiments, the isolated platelet concentrate has a volume of about 50-75 mL. In some embodiments, the isolated platelet concentrate has a volume of about 45-55 mL. In some embodiments, the isolated platelet concentrate has a volume of about 50-80 mL, about 50-70 mL, about 50-65 mL, about 50-60 mL about 50-55 mL, about 45-50 mL, about 45-55 mL, about 45-60 mL, about 45-65 mL, about 45-70 mL, about 45-75 mL, about 55-60 mL, about 55-65 mL, about 55-70 mL, about 55-75 mL, about 55-80 mL, about 60-65 mL, about 60-70 mL, about 60-75 mL, about 60-80 mL, about 65-70 mL, about 65-75 mL, about 65-80 mL, about 70-75 mL, about 70-80 mL, or about 75-80 mL. In some embodiments of the aforementioned methods, the isolated platelet concentrate has a volume of about 15-45 mL. In some embodiments, the isolated platelet concentrate has a volume of about 15-25 mL. In some embodiments, the isolated platelet concentrate has a volume of about 25-35 mL. In some embodiments, the isolated platelet concentrate has a volume of about 15-20 mL, about 15-30 mL, about 15-35 mL, about 15-40 mL, about 20-25 mL, about 20-30 mL, about 20-35 mL, about 20-40 mL, about 20-45 mL, about 25-30 mL, about 25-40 mL, about 25-45 mL, about 30-35 mL, about 30-40 mL, about 30-45 mL, about 35-40 mL, about 35-45 mL or about 40-45 mL. In some embodiments of the aforementioned methods, the isolated platelet concentrate has a volume of less than about 5 mL.

In some of the aforementioned methods, the method further comprises processing the isolated platelet concentrate unit to provide a platelet concentrate unit for pathogen inactivation and/or storage. In some embodiments of the aforementioned methods, the isolated platelet concentrate unit is further processed by addition of an additive solution (e.g., platelet additive solution, PAS) to provide a PAS platelet concentrate unit (e.g. a PAS platelet concentrate unit for pathogen inactivation and/or storage). In some embodiments of the aforementioned methods, the method further comprises adding an additive solution (e.g., platelet additive solution, PAS) to the isolated platelet concentrate to provide a PAS platelet concentrate unit (e.g. for pathogen inactivation and/or storage). In some embodiments of the aforementioned methods, the isolated platelet concentrate is a PAS platelet concentrate unit (e.g. for pathogen and/or storage) that further comprises an additive solution (e.g., platelet additive solution, PAS). In some embodiments, the PAS platelet concentrate unit comprises about 5 to 50% plasma and about 95 to 50% additive solution. In some embodiments, the PAS platelet concentrate unit comprises about 30-50% plasma. In some embodiments, the PAS platelet concentrate unit comprises about 5-10%, about 5-15%, about 51-20%, about 5-25%, about 5-30%, about 5-35%, about 5-40%, about 5-45%, about 10-15%, about 10-20%, about 10-25%, about 10-30%, about 10-35%, about 10-40%, about 10-45%, about 10-50%, about 15-20%, about 15-25%, about 15-30%, about 15-35%, about 15-40%, about 15-45%, about 15-50%, about 20-25%, about 20-30%, about 20-35%, about 20-40%, about 20-45%, about 20-50%, about 25-30%, about 25-35%, about 25-40%, about 25-45%, about 25-50%, about 30-35%, about 30-40%, about 30-45%, about 35-40%, about 35-45%, about 35-50%, about 40-45%, about 40-50% or about 45-50% plasma. In some embodiments, the PAS platelet concentrate unit comprises greater than 95% additive solution. In some embodiments, the PAS platelet concentrate unit comprises greater than 50%, 55%, 60%, 65%, 70%, 75%, 80%, 85% or 90% additive solution. In some embodiments, the additive solution is a platelet additive solution.

In some embodiments of the aforementioned methods, the method further comprises storing the isolated platelet concentrate unit for a period of about 2 hours to about 7 days. In some embodiments of the aforementioned methods, the method further comprises storing the isolated platelet concentrate unit for a period of about 2 hours to about 5 days. In some embodiments, the isolated platelet concentrate is stored for about 2 hours. In some embodiments, the isolated platelet concentrate is stored for about 1 hour, about 3 hours, about 4 hours, about 5 hours, about 6 hours, about 7 hours, about 8 hours, about 10 hours, about 12 hours, about 14 hours, about 16 hours, about 18 hours, about 20 hours, about 22 hours or about 24 hours. In some embodiments, the isolated platelet concentrate is stored for about 1 day. In some embodiments, the isolated platelet concentrate is stored for about 2 days, about 3 days, about 4 days or about 5 days. In some embodiments, the isolated platelet concentrate is stored for about 6 days or about 7 days. In some embodiments, the isolated platelet concentrate is stored with agitation. In some embodiments, the isolated platelet concentrate unit is stored for an initial period without agitation and subsequent period with agitation.

In some embodiments of the aforementioned methods, the method comprises pooling 7-12 isolated platelet concentrate units (e.g., to prepare a pooled platelet product). In some embodiments of the aforementioned methods, the method comprises pooling 7 or 8 isolated platelet concentrate units. In some embodiments of the aforementioned methods, the method comprises pooling 7 isolated platelet concentrate units. In some embodiments of the aforementioned methods, the method comprises pooling 8 isolated platelet concentrate units. In some embodiments, the pooled platelet product comprises about $1.0 \times 10^{11}$ to about $8 \times 10^{11}$ platelets. In some embodiments, the pooled platelet product comprises about $2.0 \times 10^{11}$ to about $7.0 \times 10^{11}$ platelets. In some embodiments, the pooled platelet product comprises about $2.5 \times 10^{11}$ to about $4.0 \times 10^{11}$ platelets. In some embodiments, the pooled platelet product comprises about $4.0 \times 10^{11}$ to about $6.4 \times 10^{11}$ platelets. In some embodiments, the pooled platelet product comprises about $4.0 \times 10^{11}$ to about $7.0 \times 10^{11}$ platelets. In some embodiments, the pooled platelet product comprises about $6.0 \times 10^{11}$ to about $7.0 \times 10^{11}$ platelets. In some embodiments, the pooled platelet product has a platelet concentration of about $0.5 \times 10^9$/mL to about $2.0 \times 10^9$/mL. In some embodiments, the pooled platelet product has a platelet concentration of about $0.7 \times 10^9$/mL to about $1.7 \times 10^9$/mL. In some embodiments, the pooled platelet product has a platelet concentration of about $0.7 \times 10^9$/mL to about $1.5 \times 10^9$/mL. In some embodiments, the pooled platelet product comprises at least about $6.0 \times 10^{11}$ platelets. In some embodiments, the pooled platelet concentrate units are ABO blood group matched. In some embodiments, the pooled platelet concentrate units are from the same selected subset of units. In some embodiments, the pooled platelet concentrate units are from more than one selected subset of units. In some embodiments, the at least seven isolated platelet concentrate units are from the same selected subset. In some embodiments, the at least seven isolated platelet concentrate units are from different selected subsets. In some embodiments, the at least seven isolated platelet concentrate units are from at least two, at least three or at least four different selected subsets. In some embodiments, the double dose platelet product comprises at least about $1 \times 10^{11}$, at least about $2 \times 10^{11}$, or at least about $3 \times 10^{11}$ platelets per storage container.

In some embodiments of the aforementioned methods, the whole blood donation time is less than about 15 minutes, or less than about 12 minutes, or less than about 10 minutes. In some embodiments of the aforementioned methods, the method is performed immediately after whole blood collection. In some embodiments of the aforementioned methods, the whole blood unit is stored for a period of time prior to processing. In some embodiments of the aforementioned methods, the whole blood unit is stored for a period of time prior to initiating the method. In some embodiments, the whole blood unit is stored for at least 1 hour, at least 2 hr, at least 3 hr, at least 4 hr, at least 5 hr, at least 6 hr, at least 7 hr, at least 8 hr or more, or overnight. In some embodiments, the whole blood unit is stored for less than 24 hours. In some embodiments, the whole blood unit is stored for less than 8 hours. In some embodiments, the whole blood unit is stored for at least 8 hr and less than 24 hr. In some embodiments, the whole blood unit is stored at room temperature. In some embodiments of the aforementioned methods, the donated whole blood units comprise an anticoagulant. In some embodiments, the anticoagulant is CPD or CP2D.

In some embodiments of the aforementioned methods, the method is performed (e.g., initiated) at least 1 hour, at least 2 hours, at least 3 hours, at least 4 hours, at least 5 hours, at least 6 hours, at least 7 hours, at least 8 hours or more after collection of the donated whole blood units. In some embodiments, the method is performed less than 24 hours after collection of the donated whole blood units. In some embodiments, the method is performed less than 8 hours after collection of the donated whole blood units. In some embodiments, the method is performed more than 8 hours and less than 24 hours after collection of the donated whole blood units. In some embodiments, the method is performed after an overnight storage of the donated whole blood units.

In some embodiments of the aforementioned methods, the donated whole blood units are cooled from their initial post-collection temperature. In some embodiments, the whole blood units are cooled to room temperature following donation. In some embodiments, the whole blood units are cooled to 18-25° C. following donation. In some embodiments, the whole blood units are cooled to 20-24° C. following donation.

In some embodiments of the aforementioned methods, the method further comprises treating with a pathogen inactivation compound to inactivate pathogens, if present. In some embodiments, the pathogen inactivation compound is a photoactive pathogen inactivation compound selected from the group consisting of a psoralen, an isoalloxazine, an alloxazine, a phthalocyanine, a phenothiazine, a porphyrin, and merocyanine 540. In some embodiments, the pathogen inactivation compound is a psoralen. In some embodiments, the pathogen inactivation compound is amotosalen. In some embodiments of the aforementioned methods, the method further comprises a leukoreduction step. In some embodiments, the leukoreduction step is a filtration step.

DESCRIPTION OF THE DRAWINGS

FIG. 1 illustrates average hematocrit values for female and male whole blood donors with calculation of the hematocrit of the whole blood units from whole blood volume of the unit and hematocrit of the donor.

FIG. 2 illustrates four selected subsets based on the parameters of whole blood volume and donor hematocrit values, with calculation of the hematocrit of the whole blood units from whole blood volume of the unit and hematocrit of the donor.

FIG. 3 illustrates two selected subsets based on the parameters of whole blood volume and donor hematocrit values, with calculation of the hematocrit of the whole blood units from whole blood volume of the unit and hematocrit of the donor.

DETAILED DESCRIPTION OF THE INVENTION

The term "platelet product", "platelet-containing product" or "platelet-containing blood product" means any blood derived product comprising platelets as the primary therapeutic component. Platelets are cells necessary for the coagulation of blood, and such platelet-containing blood products as described herein may be transfused to patients in need thereof, such as for patients with bleeding due to thrombocytopenia, platelet dysfunction, or while undergoing surgery. Such platelet products can be further comprised of blood plasma, anticoagulant solution used during collection, and alternatively, or in addition, a suitable storage solution, such as an additive solution, such as for example a platelet additive solution. Since other cells present in the donated blood are not completely removed, platelet-containing blood products will also contain some levels of red blood cells and white blood cells, along with plasma components. As the cellular components of the platelet product are generally a very small percentage of the volume, as is any anticoagulant solution, the platelet product is typically referred to by the composition of plasma and any platelet additive solution (PAS), if present. Worldwide the collecting and storage of platelet products varies, in that the platelets may be collected and stored in various volumes and amounts, as well as in various media, ranging from essentially 100% plasma to a percentage of plasma and a percentage of a suitable storage media, such as for example 35% plasma and 65% suitable PAS.

A "pooled platelet product", as used herein refers to a platelet product prepared from platelets (e.g., RDP) obtained from more than one whole blood or other donation and subsequently combined (e.g., in a single container) prior to final product use, such as before transfusion. Generally, the blood donations are obtained from different donors. Platelets may be pooled at any stage after blood donation and prior to final product use, including but not limited to pooling as platelet rich plasma or as platelet concentrate, before or after any addition of additive solution, before or after any storage period, and before or after any pathogen inactivation processing.

A "pathogen inactivated platelet product" as used herein describes a platelet product that has undergone processing (e.g., by the methods described herein) to inactivate pathogens that may be present in a unit of platelets, where it is understood that the process does not necessarily inactivate completely all pathogens that may be present, but substantially reduces the amount of pathogens to significantly reduce the risk of a transfusion associated disease. The inactivation of a pathogen may be assayed by measuring the number of infective pathogen (e.g., viral or bacterial particles) in a certain volume, and the level of inactivation is typically represented in the log reduction in the infectivity of the pathogen, or log reduction in titer. Methods of assaying log reduction in titer, and measurements thereof for pathogen inactivation are known in the art. When the inactivation process is tested against a variety of pathogens, the reduction in a particular active pathogen is at least about 1 log, at least about 2 log, at least about 3 log, at least about 4 log, or at least about 5 log reduction in titer. Such pathogen inactivated platelet product, in addition to use for transfusion into a subject in need thereof, may also be further processed for other uses, for example the unit can be further processed to provide a platelet lysate product.

The term "unit of platelets" or "platelet unit" means any platelet-containing solution for processing, where such processing is used in the production of a platelet-containing blood product, such as for example to provide a pathogen inactivated platelet product. The distinction between a platelet product and a unit of platelets is that the unit of platelets is processed by the methods as described herein or similar methods as known in the art to become a platelet product. Effectively, a product is ready for use, or suitable for transfusion while a unit of platelets requires additional processing, such as pathogen inactivation or removal of pathogen inactivation compound. A unit of platelets can be from any source of platelets such as apheresis, or platelets from blood donations, where it is not limited to a single unit, or pooled multiple units, but could also be, for example, a portion of a double or triple sized apheresis unit. Essentially, a unit of platelets is a quantity of platelets in suitable media that is contained within a single container (e.g. one blood bag) during a processing step in the production of a platelet product (e.g., pathogen inactivated platelet product), for example including a photoactivation step during pathogen inactivation, or a subsequent compound removal step as described herein. A unit of platelets that has undergone pathogen inactivation (i.e., contained within a single container) may be more specifically referred to as a "pathogen inactivated unit of platelets" When such a unit has had the concentration of pathogen inactivation compound reduced to a desired concentration, the unit is separated from the removal device in transferring to a product container to provide the pathogen inactivated platelet product.

The term "pathogen inactivated unit of platelets" or "pathogen inactivated platelet-containing blood product" or "pathogen inactivated platelet product" or similar terms, means a platelet-containing blood product or unit of platelets that has been treated to inactivate pathogens that may be present, thereby providing a unit of platelets or ultimately platelet product having a reduced risk of transfusion associated disease when infused into a patient. It is understood that pathogens that may be present are substantially inactivated by a treatment method, so that the risk of a transfusion associated infection is significantly reduced. It does not mean that all pathogens that may be present are completely inactivated, only that inactivation is sufficient for reducing this risk. For example, the inactivation of a pathogen is assayed by measuring the number of infective viral or bacterial particles in a certain volume, and the level of inactivation is typically represented in the log reduction in the infectivity of the pathogen, or log reduction in titer. Methods of assaying log reduction in titer, and measurements thereof for pathogen inactivation are described, for example, in U.S. Pat. No. 7,655,392, the disclosure of which is hereby incorporated by reference as it relates to assays for pathogen inactivation. As such, for any given pathogen, known amounts can be added to a test unit of platelets to assess how much inactivation results from the process, where typically the pathogen inactivation process results in at least about 1 log reduction in titer, or about 2 log, about 3 log, about 4 log, or at least about 5 log reduction in titer.

While the methods as described herein are applicable to any pathogen inactivation treatment, it is desirable that a variety of pathogens assessed by the process are inactivated to at least 1 log reduction in titer, including a pathogen selected from the group consisting of HIV-1, HBV, HCV, HTLV-1, HTLV-2, West Nile virus, *Escherichia coli*, *Klebsiella pneumoniae*, *Yersinia enterocolitica*, *Staphylococcus epidermidis*, *Staphylococcus aureus*, *Treponema pallidum*, *Borrelia burgdorferi*, *Plasmodium falciparum*, *Trypanosoma cruzi*, and *Babesia microti*.

The term "platelet additive solution" means any suitable aqueous composition that can be used in the storage of a platelet product. Such platelet additive solutions typically provide nutrients and buffering capacity to allow for extended storage of platelets while maintaining suitable platelet function. A variety of suitable platelet additive solutions may be used in the storage of platelets, where such solutions can be added to a unit of platelets in various amounts, such that a unit of platelets may comprise anywhere from about 0 to 95% platelet additive solution, about 5 to 95% platelet additive solution, about 50 to 95% platelet additive solution, about 50 to 75% platelet additive solution, about 53% to 70% platelet additive solution, or about 53 to 68% platelet additive solution. For example, platelets may be stored in about 65% platelet additive solution and about 35% plasma, providing a unit of platelets comprising platelets, about 65% platelet additive solution, and about 35% plasma. Typically, in the methods described herein, a unit of platelets will be prepared to a desired level of plasma by addition of the platelet additive solution, either automatically in apheresis collection, or manually in the processing of platelet rich plasma or buffy coat platelets. Platelet additives for use herein are described in terms of their aqueous concentration of components prior to their addition to the platelets to give the desired level of plasma in the additive containing unit of platelets. Thus, for a platelet additive solution described as having, for example, an acetate concentration of X μM, when used to provide a platelet unit at 65% platelet additive solution and 35% plasma, will have an acetate concentration of 0.65X μM (not including any amount of acetate that may be present in the plasma). Platelet additive solutions typically include sodium chloride and one or more components selected from the group consisting of citrate, phosphate, acetate, magnesium, potassium, calcium, gluconate, glucose, and bicarbonate. The following examples comprise sodium chloride and the indicated components: PAS-A (also referred to as PAS(1)) comprising citrate, phosphate and potassium; PAS-B (also referred to as PAS II, PAS-2, SSP, or T-Sol) comprising citrate and acetate; PAS-C (also referred to as PAS III, PAS-3, or Intersol) comprising citrate, phosphate, and acetate; PAS-D (also referred to as Composol) comprising citrate, phosphate, acetate, magnesium, potassium, and gluconate; PAS-E (also referred to as PAS IIIM or SSP+) comprising citrate, phosphate, acetate, magnesium, and potassium; PAS-F (also referred to as PlasmaLyte A) comprising acetate, magnesium, potassium, and gluconate; PAS-G comprising citrate, phosphate, acetate, magnesium, potassium, and glucose; InterSol-G (also referred to as PAS IV) comprising citrate, phosphate, acetate, magnesium, potassium, calcium and glucose; Isoplate (also referred to as Isolyte S) comprising phosphate, acetate, magnesium, potassium, and gluconate; PAS V comprising citrate, acetate, phosphate, magnesium, potassium, calcium, glucose, and bicarbonate; and M-Sol comprising citrate, acetate, magnesium, potassium, calcium, glucose and bicarbonate. Detailed composition of these platelet additive solutions is found in the following Tables 1a and 1b. Preferred platelet additive solutions for use in the examples described herein include SSP+ (PAS-E) and InterSol (PAS-C). The composition of SSP+ is 69 mM sodium chloride, 30 mM sodium acetate, 10 mM trisodium citrate, 26 mM sodium phosphate, 5 mM potassium chloride, and 1.5 mM magnesium chloride or magnesium sulfate. The composition of InterSol is 77 mM sodium chloride, 33 mM sodium acetate, 11 mM trisodium citrate, and 28 mM sodium phosphate.

Tables 1a and 1b: composition of platelet additive solutions.

| | Platelet additive solution component concentration (mM) | | | |
|---|---|---|---|---|
| Component | PAS-B | PAS-C | PAS-D | PAS-E |
| NaCl | 116 | 77 | 90 | 69 |
| Acetate | 30 | 33 | 27 | 30 |
| Citrate | 10 | 11 | 11 | 10 |
| Phosphate | 0 | 28 | 0 | 26 |
| Gluconate | 0 | 0 | 23 | 0 |
| K$^+$ | 0 | 0 | 5 | 5 |
| Mg$^{2+}$ | 0 | 0 | 1.5 | 1.5 |

| | Platelet additive solution component concentration (mM) | | | | |
|---|---|---|---|---|---|
| Component | PAS-F | Isoplate | InterSol-G | PAS V | M-Sol |
| NaCl | 90 | 92.7 | 69.8 | 69.4 | 77 |
| Acetate | 27 | 27.2 | 30 | 30 | 21 |
| Citrate | 0 | 0 | 10 | 10 | 9.4 |
| Phosphate | 0 | 0.5 | 9.6 | 9.4 | 0 |
| Gluconate | 23 | 22.9 | 0 | 0 | 0 |
| K$^+$ | 5 | 5 | 5 | 5 | 3 |
| Mg$^{2+}$ | 3 | 1.5 | 1.5 | 1.5 | 1.6 |
| Ca$^{2+}$ | 0 | 0 | 1 | 1 | 1 |
| Glucose | 0 | 0 | 18.5 | 16.8 | 15 |
| Bicarbonate | 0 | 0 | 0 | 9 | 43.5 |

The term "pathogen inactivation compound" means any suitable compound, such as a small organic compound, that can be used to inactivate a pathogen that may be present in a platelet-containing blood product. A "photoactivated pathogen inactivation compound" is a suitable compound that requires some level of light in order to sufficiently inactivate a pathogen. Such compounds are preferred in the inactivation of pathogens in platelet products as they provide control over the inactivation process. Such photoactivated pathogen inactivation compounds described herein include psoralens, isoalloxazines, alloxazines, phthalocyanines, phenothiazines, and porphyrins, where these terms are understood to encompass a general class of compounds, i.e. the core compound and suitable derivatives thereof. For example psoralens or a psoralen generally describes the psoralen core compound and any derivative thereof (e.g. amotosalen), isoalloxazines or an isoalloxazine generally describes the isoalloxazine core and any derivative thereof (e.g. riboflavin), and so forth. Such derivatives comprise the core compound structure as well as additional substituents on the core. Descriptions of such compounds include any salts thereof.

The term "amotosalen" means the compound 3-(2-aminoethoxymethyl)-2,5,9-trimethylfuro[3,2-g]chromen-7-one and any salts thereof. The compound may also be referred to as 3-[(2-aminoethoxy)methyl]-2,5,9-trimethyl-7H-furo[3,2-G][1]benzopyran-7-one-hydrochloride. The compound may also be referred to as 4'-(4-amino-2-oxa)butyl-4,5',8-trimethyl psoralen. Where the inactivation of platelets includes adding amotosalen HCl (the HCl salt of amotosalen) to a unit of platelets, the removal of this compound from the unit of platelets is not limited to the removal of amotosalen HCl, as the amotosalen can be present in solution as other salts or as the free base. As used in the methods described herein, removal of amotosalen means removal of the compound in any form, e.g. as the free base or as any salt, as measured by the assays described herein. Treatment or processing of platelets by amotosalen inactivation refers to combining platelets (e.g., unit of platelets, individual unit, pooled) with amotosalen and illuminating with a suitable dose of UVA light in order to inactivate pathogens that may be present in the platelets. In some embodiments, amotosalen inactivated platelets have been pathogen inactivated according to commercial methods for platelets, or by similar methods. Such methods provide, for example, a platelet unit prior to addition of amotosalen having a volume within the range of 255 to 420 mL, a total platelet content in this volume of 2.5 to $8.0 \times 10^{11}$, where the platelet unit is in 100% plasma, or 32 to 47% plasma with the remaining volume platelet additive solution (i.e. 53 to 68% PAS, where % plasma+% PAS=100), which is combined with either 15 mL or 17.5 mL of a 3 mM amotosalen solution, resulting in a platelet unit ready for illumination having an amotosalen concentration within the range of about 120 to 193 µM prior to illumination. In some areas, such as Japan, it is desirable to process a smaller volume platelet unit. Here a platelet unit may be provided having a volume in the range of 160 to 300 mL volume, with the platelet content ranging from about 2.0 to $4.5 \times 10^{11}$ platelets, where the platelet unit is in 100% plasma, or 32 to 47% plasma with the remaining volume platelet additive solution, which is combined with about 15 mL of a 2.25 mM amotosalen solution or about 30 mL of a 1.2 mM amotosalen solution to provide the unit ready for illumination. The resulting solution is illuminated with the equivalent of about 3 J/cm$^2$ of light in the UVA wavelength range. In current practices, platelet units are treated under the following guidelines for a small volume set (with PAS), large volume set (with PAS or 100% plasma) and dual storage set (with PAS) as shown in Table 2, wherein the present invention is designed to significantly reduce the removal device incubation time for each of these configurations. While the methods described herein are applied to platelet units using known systems such as the use of amotosalen for pathogen inactivation in platelets, they are applicable to any pathogen inactivated unit of platelets.

TABLE 2

Parameters for the preparation of pathogen inactivated platelets using amotosalen in 100% plasma or including PAS.

| | Small Volume | Large volume Suspension medium | | Dual Storage |
| --- | --- | --- | --- | --- |
| | PAS | PAS | No PAS | PAS |
| Platelet content | $2.5\text{-}6.0 \times 10^{11}$ | $2.5\text{-}7.0 \times 10^{11}$ | $2.5\text{-}7.0 \times 10^{11}$ | $2.5\text{-}8.0 \times 10^{11}$ |
| Volume | 255-325 mL | 300-420 mL | 255-390 mL | 300-420 mL |
| Plasma | 32-47% | 32-47% | 100% | 32-47% |
| CAD time | 4-16 hrs | 6-16 hrs | 16-24 hrs | 6-16 hrs |

The term "sufficient biological activity to be suitable for infusion into a human" or similar terms, as used herein refers to a platelet product prepared by the methods as described herein wherein the platelet product has sufficient biological activity for its intended use, i.e., for use where a transfusion of human platelets is indicated, such as for patients with bleeding due to thrombocytopenia, platelet dysfunction, or while undergoing surgery. The photoactivation of pathogens in platelet units using amotosalen is well established to provide such a platelet product that is suitable for transfusion into humans. The suitability of such a unit of platelets is evidenced by having a pH measured at 22° C. within a desired range, for example in the range of 6 to 7.8, or 6.2 to 7.6. While it is sufficient to assess the platelets by measuring the pH, there are a number of biological characteristics of the platelet product that can also be assessed to evaluate the quality of the unit for infusion into a human, including, but not limited to platelet integrity assessed by platelet count and supernatant LDH, lactate concentration, platelet content, platelet morphology score, glucose concentration, platelet aggregation, extracellular adenosine triphosphate concentration, total adenosine triphosphate concentration, extent of shape change, and platelet hypotonic shock response. It may be desirable to also look at the extent of shape change and hypotonic shock response in addition to pH when evaluating the condition of the pathogen inactivated platelets as described herein (Holme, S. et al., Transfusion 1998, 38:31-40).

The term "under sterile conditions" as used herein refers to maintaining the sterility of the system, for example by connection of two bags from a blood processing set, or refers to a means by which the process does not introduce contamination. For example, as used in the methods described herein, a source unit of platelet comprising a tubing for connection to a processing set or container of pathogen inactivation compound comprising a similar tubing may be joined under sterile condition by methods known in the art, for example using a sterile connect device, which acts to melt or weld the tubing together to provide a flow path between the two containers that is sterile. Similarly, when methods described herein describe sealing off such tubing, the sealing is done under sterile conditions, for example using a tubing welder.

A "blood-collection bag" can be any bag used for collecting blood from a donor as known in the art. Blood collected in a blood-collection bag that is not attached to other bags is centrifuged to separate the blood into blood components. Then, the blood-collection bag is sterile docked to a number of satellite bags that corresponds to the number of blood products it has been determined to manufacture from the whole blood. Blood in a blood-collection bag may be processed, such as by centrifuging, in the blood-collection bag before separation into satellite bags, or the blood may be transferred (by gravity or by pumping) from the blood-collection bag to a blood-processing bag.

A "blood-processing bag" is any such bag known in the art, other than the blood-collection bag, used for processing blood. The blood-processing bag may be preconnected to the blood-collection bag or attached to the blood-collection bag through sterile docking. Blood transferred to a blood-processing bag is centrifuged. Prior to centrifuging or immediately after centrifuging, the blood-processing bag is sterile docked to a number of satellite bags that corresponds to the number of blood products it has been determined to manufacture from the whole blood.

Blood Collection and Sampling

Whole blood for use in the preparation of platelets as described herein may be collected by a variety of procedures known in the art. One of the most common blood collection techniques, is the "manual" collection of whole blood from healthy donors. As commonly understood and as used herein, manual collection refers to a collection method where whole blood is allowed to drain from the donor and into a collection container without the use of external pumps or similar devices. This is in contrast to so-called automated procedures where blood is withdrawn from a donor and further processed by an instrument that typically includes a processing or separation device and pumps for moving blood or blood components into and out of the device.

Regardless of whether the blood collection technique is manual or automated, withdrawing blood from the donor typically includes inserting a vein access device, such as a needle, into the donor's arm (and, more specifically, the donor's vein) and withdrawing blood from the donor through the needle. The "venipuncture" needle typically has attached to it, one end of a plastic tube that provides a flow path for the blood. The other end of the plastic tube terminates in one or more pre-attached plastic blood containers or bags for collecting the blood. The needle, tubing and containers make up a blood collection set which is pre-sterilized and disposed of after a single use. The sterile blood collection container typically serves as the primary container for initial separation of platelet rich plasma (PRP) from red blood cells.

The blood collection container and plastic tubing may also include a volume of a liquid anticoagulant, while in the automated technique, a separate container of anticoagulant may be provided from which the anticoagulant is metered into the flow path and mixed with the incoming whole blood. Anticoagulant is required because of the tendency of blood to clot and adhere to the walls of the plastic surfaces which it. Exemplary anticoagulants are well known in the art and may include, but are not limited to, an anticoagulant citrate phosphate dextrose (CPD) solution, an anticoagulant citrate phosphate double dextrose (CP2D) solution, an anticoagulant citrate phosphate dextrose adenine (CPDA) solution (e.g., CPDA-1), an acid citrate dextrose (ACD) solution (e.g., ACD-A), and an anticoagulant sodium citrate 4% w/v solution.

Blood may be identified or characterized with respect to one or more parameters, such as for example, hematocrit, hemoglobin, donor gender, whole blood volume, packed cell volume and/or platelet count. Such identification or characterization is typically prior to or shortly after blood collection, but prior to subjecting the collected whole blood to further processing, such as according to the methods provided herein. In addition, at or near the time of collection and prior to transfusion to a patient, tests may be performed for determining blood type and the presence of pathogens such as virus, bacteria and/or other foreign substances in the donor's blood. Such testing generally requires obtaining a sample of the donor's blood. Generally sampling of blood may be before, during or after donation, but without compromising the sterility of the system and/or the collected blood product. For example, samples may be commonly obtained by finger stick, heel stick or venipuncture. In the case where blood for hemoglobin testing is gathered with a capillary stick, a single-use sterile lancet may be used. Another well-known technique is to simply withdraw or collect the blood remaining in the flow path of the collection set after donation. This involves removing the needle from the donor, inserting the needle into a vacuum sealed sampling vial or tube and allowing the blood from the flow path to drain into the vial. Another alternative is to clamp off the flow path near the collection container and divert the blood being withdrawn from the donor to a collection (sampling) vial or tube. This procedure may employ a particular type of disposable tubing set having a pre-attached sampling site on the main flow path. Blood at or near the sampling site may be obtained by piercing the sampling site with a separately provided needle or other piercing device, and attaching a sampling vial thereto. To minimize the risk that the incoming blood will be exposed to the outside environment, the sample is typically collected after completion of the blood donation. Alternatively, some collection bags or collection sets include diversion pouches to sequester a portion (e.g., the first 20 ml) of blood collected. Another example of a blood sampling system is described in U.S. Pat. No. 5,167, 656, which describes blood collection sets with an enlarged sample collection portion included in the flow path. Blood for sampling is collected in the enlarged portion by clamping off the flow path near the collection container and allowing the enlarged tubing portion to fill with blood.

For each of the parameters set forth in the methods provided herein, techniques for determination or measurement of the parameters are well known in the art.

Hematocrit (HCT) is generally similar to packed cell volume (PCV), and refers to the fraction or percentage of whole blood volume that consists of red blood cells, and is typically expressed as L/L units. Hematocrit may also be expressed as percentage (%). While not expressed as a fraction or percentage of whole blood volume, quantitation of red blood cell count in whole blood (e.g., as quantity× $10^{12}$/L) can provide similarly useful information as hematocrit and packed cell volume for purposes of the methods of the present disclosure, and thus may be considered an optional alternative parameter. Hematocrit may be measured by any method known in the art. For example, a common measurement technique is using a microcapillary tube. A drop of blood obtained in a microhematocrit capillary tube may be centrifuged for 5 minutes at >10,000 g to pellet the red blood cells. After centrifugation, the height of the red cell column is measured and compared to the total height of the column of whole blood. The percentage or fraction of the total blood volume occupied by the red cell mass is the hematocrit. Hematocrit depends primarily on the number of red blood cells.

Hemoglobin is a protein contained in red blood cells that is responsible for delivery of oxygen to the tissues. The amount of hemoglobin in whole blood is typically expressed in grams per deciliter (g/dL). The normal Hb level for males is generally considered to be 14 to 18 g/dL; and that for females is generally considered to be 12 to 16 g/dL. Several methods exist for measuring hemoglobin, most of which utilize automated blood analysis machines. For example, within automated cell counters, the red blood cells are broken down to release the hemoglobin into solution. The free hemoglobin is exposed to a cyanide-containing chemical which binds tightly with the hemoglobin molecule to form cyanomethemoglobin, which is measured by colorimeter (e.g., at a wavelength of 540 nanometers). For a parameter such as, for example, hemoglobin, where different units may be used (e.g., conventional units as g/dL and SI units as mmol/L), it should be understood that where the present disclosure provides a quantity designated in one unit, another unit may be interchanged by use of a conversion factor. For example, conversion factors may be used for hemoglobin units and include, for example, conversion from g/dL to mmol/L hemoglobin (multiply g/dL by 0.621), or from mmol/L to g/dL hemoglobin (multiply mmol/L by 1.611).

Whole blood volume is generally a function of the size of the blood collection bag, with certain ranges that can be accommodated within each size of collection bag. Typically, whole blood volume is determined not by direct volume measurement, but rather by weighing the bag pre- (tare weight) and post-collection to determine the weight of the whole blood contents, and then calculating the total volume based on a specific gravity conversion factor (e.g., 1.056 g/L). Any added anticoagulant or other solutions present may be subtracted from the total volume, if desired, to determine the collected whole blood volume.

Quantitation to determine platelet count may be performed using standard techniques known in the art, including either manual techniques, for example, using a Neubauer counting chamber, or automated techniques, for example, using a commercially available automated cell counter (MS 4 Melet Schloesing Laboratories, France).

Whole blood units may be held at room temperature following collection. Whole blood units may also be cooled from their initial post-collection temperature, for example using any of a number of available standard cooling plates or other devices. For example, whole blood units may be cooled to room temperature, or a temperature within the range of 18-25° C., or 20-24° C., and may be maintained at such lower temperature until further processing.

Whole blood units may be subjected to one or more of the methods disclosed herein immediately after collection (e.g., as soon as possible, without delay), or alternatively the whole blood units may be "rested" or stored for a period of time prior to processing according to the method(s) described (e.g., prior to initiating the method(s)). For example, whole blood units may be stored after collection for at least 1 hour, at least 2 hr, at least 3 hr, at least 4 hr, at least 5 hr, at least 6 hr, at least 7 hr, at least 8 hr or more, or overnight before subjecting the whole blood to the method(s) of the present disclosure. In one embodiment, the whole blood is stored for less than 24 hours (e.g., 0-24 hr) after collection before subjecting to the method(s) of the present disclosure. In another embodiment, the whole blood is stored for less than 8 hours (e.g., 0-8 hr) after collection before subjecting to the method(s) of the present disclosure. In another embodiment, the whole blood is stored for at least 8 hr and less than 24 hr after collection before subjecting the whole blood to the methods disclosed herein.

Platelet Processing

Platelet processing and the handling of blood products typically involves the use of blood bag systems, which are well known in the art, as described, for example, in U.S. Pat. No. 5,405,343, U.S. Pat. No. 7,025,877, and U.S. Pat. No. 8,439,889, the disclosures of which are incorporated by reference herein for the disclosure of blood handling bags and systems. In general, a blood handling system includes more than one plastic container, typically plastic bags, where the bags are integrally connected with plastic tubing. Some of the containers described herein include such plastic bags as are known in the storage and handling of blood products, including platelet products. Blood bags typically can be designed to hold various volumes of fluid, including, but not limited to, volumes ranging from 50 mL to 2 liters, for example having up to a 1 liter capacity, up to a 1.5 liter capacity, or up to a 2 liter capacity. Examples of common blood-collection bags include such bags with volumes of 350 mL, 450 mL and 500 mL, among others. It is understood that when a method refers to a bag, it includes any such plastic bags used in blood handling. Where such bags are referred to as "removal bag", "product bag", or "illumination bag", it is understood that these bags are typical blood handling bags, or are similar to such bags in nature. Plastic bags suitable for use according to the present disclosure include for example, those comprising PL2410, as well as other suitable plastics known in the art. Plastic bag materials include polyvinyl chloride, polyolefins, ethylene vinyl acetate, ethylene vinyl acetate blended with other plastics, and the like.

As described herein, where tubing is described as connecting e.g. two bags of a processing set, it is understood that the tubing may be joined at some point therebetween by another component of the connection between the two bags. For example, a removal bag connected to a product bag by a tubing includes wherein the tubing comprises a filter between the two bags, i.e. the tubing is divided by a filter such that fluid flows from one bag to the other through the tubing and filter. In one example, tubing connecting a removal bag and a product bag can include a filter to remove any loose particles from fluid flowing from the removal device to the product bag, i.e. the tubing is divided by, or interrupted by the filter between the bags. Such filters are designed to remove any small particles that may come off of the removal device, while allowing platelets to pass through the filter. The tubing between bags allows for fluid to flow from one bag to another, which can be blocked to prevent the flow until necessary, e.g. as part of the processing the fluid in one bag may be prevented from flowing to the next bag until required for the next step in a process. As such an openable seal, such as a clamp, plug, valve or the like is included in or on the tubing connecting the bags, where the clamp, plug, valve or the like can be selectively opened as required, for example to transfer the fluid from one bag to the next. In certain preferred embodiments, the tubing between bags comprises a breakable seal, such as a breakable valve, whereupon breaking the breakable seal allows for the blood solution to flow between the bags through the tubing. It is understood that the breakable seal is contained within the connection between containers, such that sterility of the system is maintained. It is also understood that a tubing comprising a filter, or a breakable seal, includes where the tubing may be interrupted by the filter or the seal, for example the tubing runs from one bag and is connected to the filter or seal (an incoming portion of the tubing), and the tubing continues from another portion of the filter or seal to another bag (an outgoing portion of the tubing). In such a configuration, fluid flows from the first bag, through the incoming portion of the tubing, through the filter or seal, and through the outgoing portion of the tubing and into the other bag.

Different bags within a blood bag system can be used for different steps of a process. For example, a system of bags to be used for the pathogen inactivation of a unit of platelets can include a container with pathogen inactivation compound contained within, a bag for receiving the unit of platelets and a pathogen inactivation compound (e.g. an illumination bag), a bag for the illumination of the unit of platelets when the pathogen inactivation method includes illumination (e.g., an illumination bag, and typically the same bag to receive the unit of platelets and pathogen inactivation compound), a bag for the removal of pathogen inactivation compounds and/or by-products thereof from the treated unit of platelets (e.g., referred to as a removal bag), and one or more bags for containing the final platelet product, i.e. the pathogen inactivated platelet unit that has the concentration of the inactivation compound and/or by-products thereof reduced to below a desired concentration, which is ready for use or can be stored for later use (e.g., referred to as a product bag). Each bag in the system is typically made up of a plastic material. For example, the container for containing a solution of pathogen inactivation compound can be made of a suitable plastic such as PL2411 (Baxter Healthcare), or other plastics such as polyvinyl chloride, polyolefins, ethylene vinyl acetate, ethylene vinyl acetate blended with other plastics, and the like. This container is also overwrapped with a material that is impermeable to light of a wavelength that will activate the photoactive pathogen inactivation compound (for example suitable plastic such as PL2420, Baxter Healthcare). The illumination bag for a photoactivated pathogen inactivation compound requires a clear, durable thermoplastic material that is translucent to light of the selected wavelength. Suitable plastics that are translucent to light in the UVA wavelength range include polyvinyl chloride, polyolefins, ethylene vinyl acetate, ethylene vinyl acetate blended with other plastics, or other blends of thermoplastic polymers. Such suitable plastics include PL2410 (Baxter Healthcare) and PL732 (Baxter Healthcare). Similar materials may be used to make the removal bag and the product bag. The product bags include those made of PL2410, or can be a Kawasumi PO-80 bag (Kawasumi Laboratories). Suitable bag materials are discussed, for example, in PCT publication number WO 2003078023, and U.S. Pat. No. 7,025,877, the disclosures of which are hereby incorporated by reference as it relates to such bag materials and related materials. In all cases, the materials used in preparing the processing set have to be sterilizable by known methods such as steam and gamma or electron beam radiation used to ensure sterility of the processing set. While these are exemplary materials for making the bags, the methods described herein are applicable to processes using any suitable bag material as would be readily available to one skilled in the art, and can also be used with containers other than bags. The bags used for illumination, removal, and storage are also designed to allow for gases such as oxygen and carbon dioxide to go into and out of the blood bag, so that the platelets therein have adequate oxygen supply and carbon dioxide levels during the processing and storage.

Preparation of Platelet Products

The PRP method of preparing platelet rich plasma and subsequently, if so desired, platelet concentrate (sometimes referred to as random donor platelets, RDP) utilizes two centrifugation steps. The first centrifugation step is performed under conditions that result in separation of the platelet rich plasma component from the red blood cell component. This centrifugation step is typically a slower, "soft" spin, intended to maintain a high percentage of the lighter platelets in the liquid plasma component, while pelleting the heavier red blood cells. A second, faster "hard" spin centrifugation step is performed to concentrate the platelets and remove the excess of plasma (platelet poor plasma) to a desired remaining volume for platelet suspension. The specific centrifugation conditions (e.g., centrifugal force, speed, time) may vary according to conditions optimized by the blood bank, for example based on the centrifuge and rotor, desired yield (e.g., platelet recovery, plasma recovery) and desired firmness of pelleted material (e.g., red blood cells, platelets).

In the present disclosure, methods of selecting subsets of whole blood units and preparing platelet products from such subsets are provided. Centrifugation conditions for improved platelet preparation may be determined by processing samples of a subset using PRP methods and varying such centrifugation inputs as, for example, RCF, RPM, time, acceleration settings, deceleration settings and the like, particularly for the first "light" centrifugation step, such as illustrated in the Examples below. Centrifugation conditions for selected subsets are determined to provide improvement in platelet preparation (e.g., platelet yield, platelet recovery, platelet quality). An improvement (e.g., optimization) in platelet preparation may be determined using any known measure or read out being evaluated. For example platelet yield or platelet recovery following platelet preparation from donor whole blood by a PRP method (e.g., PRP preparation method provided herein) may be determined by quantifying platelets in samples before, during and/or after platelet preparation, such as described below. When comparing different centrifugation conditions for a subset, one can readily determine whether a change in centrifugation input(s) has increased (improved) or decreased platelet recovery or yield. Similarly, for any known measure of platelet quality, such measures can be correlated as improving, not changing or negatively impacting platelet quality following a particular change in centrifugation input(s).

Subset selection and platelet preparation methods determined for a subset may be specific to a particular parameter upon which the subset selection is made (e.g., donor gender, hematocrit, hemoglobin, whole blood volume, packed cell volume, platelet count). Further, for a given parameter, one or more subsets may be selected within that parameter (e.g., male or female donor gender, at least two or at least three or at least four specified ranges for a parameter such as for example, hematocrit, hemoglobin and/or whole blood volume) and platelet preparation methods determined for each subset within the parameter. Thus, platelet preparation methods as disclosed herein may, in certain embodiments, depend not only on a single parameter or range within a parameter, but also on more than one selection criteria, such as for example a combination of multiple selected parameters and/or multiple selected ranges for different parameters. In addition, a specific range for a parameter generally may be narrower than the range that meets the acceptance criteria of a regulatory agency or accrediting organization for the same parameter for donated whole blood. Centrifugation conditions may be different for selected subsets of whole blood units, and such differences in centrifugation conditions may, for example, occur only in a single step within the preparation process (e.g., the first "soft" spin to separate PRP from RBCs), or may be at multiple steps within the process.

Following the initial soft spin centrifugation step, the platelet rich plasma is isolated from red blood cells using accepted blood processing practices. For example, in a manual plasma press expression method, each bag is placed in an "expressor" consisting of two rigid plates that are joined by a spring loaded hinge. One of the plates is fixed and the other is moveable. The blood bag is positioned between the two plates and the spring catch released causing the moveable plate to press against the bag. A port on the top of the bag is then opened and the platelet-rich plasma is expressed into an attached, empty bag. When the red cells are about to reach the outlet port, the expression is stopped and the tubing clamped. If platelets are to be separated from the plasma, the bags containing the platelet rich plasma are returned to the centrifuge, the load is again balanced and a second spin begins, this time at a higher speed. This spin forces the platelets to the bottom of the bag and allows the lighter plasma to rise to the top. After the second centrifugation, the PRP unit can be separated using an automated cell separator or manually, for example using a plasma press (e.g., expression), or placed on a higher part of a work bench, to remove the plasma or reduce the volume of plasma on the platelet sediment. Platelet poor plasma will be collected in a separate plasma container. Any desired amount of plasma may be maintained with the platelets (e.g., 50-70 mL). Accurate plasma volume on the platelet concentrate can be done automatically by the cell separator or by weighing.

Various volumes of plasma may be specified to remain with the platelet concentrate for the individual RDPs and different platelet product pools can be prepared out of single RDP's based on different plasma volumes and/or the addition of platelet additive solution (PAS), such as for example, as illustrated in the following table:

| Product example | Pool size | RDP (range) | RDP pool (average) | Plasma % | PAS volume (mL) |
|---|---|---|---|---|---|
| | | volume (mL) | | | |
| 1 | 4 | 65-70 | 270 | 100 | 0 |
| | 5 | 50-70 | 275 | 100 | 0 |
| 2 | 7 | 55-60 | 404 | 100 | 0 |
| | 8 | 47-52 | 400 | 100 | 0 |
| 3 | 5 | 25-34 | 400 | 33-40 | 250 |
| | 5 | 20-35 | 338 | 33-47 | 200 |
| 4 | 7 | 22-24 | 411 | 38-40 | 250 |
| | 8 | 16-21 | 398 | 34-40 | 250 |
| 5 | 8 | <5 | 400 | <1 | 400 |

Among these exemplary platelet product pools, examples 1 and 2 provide for 100% plasma and 4, 5, 7, or 8 RDP platelet concentrates, examples 3 and 4 provide for 5, 7 or 8 RDP platelet concentrates in a mixture of plasma and PAS with plasma comprising 33-47% of the volume, while example 5 provides for 8 RDP platelet concentrates suspended in primarily PAS.

While the initial centrifugation step is of particular importance, generally, the centrifugation conditions involved in current processing methods in the blood bank industry are standardized without consideration to individual whole blood units. In practice, this results in a high degree of process variability for the PRP method, which results in up to about 10% or more of units being of unacceptable quality, due to any of several factors, such as for example, contamination by red blood cells, white blood cells, platelet aggregates and/or lipids, as well as variable platelet yields that can be lower than desirable, for example recovery of platelets at about 60-80%. Additionally, this high degree of variability from the PRP method, may also adversely affect the downstream treatment of platelet preparations (e.g., platelet concentrates) in subsequent pathogen inactivation methods, which may have strict process requirements.

The present disclosure provides improved methods for obtaining platelet preparations of high quality and with high recovery (e.g., 85%, 90%, 95% or more). Generally the improved methods are achieved by identifying particular parameters in donated whole blood and selecting subsets of the whole blood units for processing under like conditions, which is contrary to the typical standardized current practices. In one aspect, the present disclosure provides a method (e.g., improved method) of preparing a platelet product comprising: a) selecting a subset of whole blood units from a plurality of donated whole blood units, wherein the plurality of donated whole blood units meet the acceptance criteria of a regulatory agency or accrediting organization for donated whole blood, wherein each unit of the subset of whole blood units is within a specified range for each of one or more parameters selected from the group consisting of hematocrit, hemoglobin, donor gender, whole blood volume, packed cell volume and platelet count, and wherein the specified range for each of the one or more parameters for the selected subset of whole blood units is narrower than the range that meets the acceptance criteria of a regulatory agency or accrediting organization for the same parameter for donated whole blood; b) centrifuging the selected subset of units under the same centrifugation conditions to provide each unit having a separated layer of platelet rich plasma; and c) isolating the separated layer of platelet rich plasma to provide a platelet rich plasma unit.

In another aspect, the present disclosure provides a method (e.g., improved method) of preparing a platelet product comprising: a) identifying a plurality of donated whole blood units according to one or more parameters selected from the group consisting of hematocrit, hemoglobin, donor gender, whole blood volume, packed cell volume and platelet count; b) selecting a subset of whole blood units from the plurality of donated whole blood units, wherein each unit of the selected subset is within one of at least two specified ranges for at least one of the one or more parameters; c) centrifuging the selected subset of units under the same centrifugation conditions to provide each unit having a separated layer of platelet rich plasma; and d) isolating the separated layer of platelet rich plasma to provide a platelet rich plasma unit.

Various parameters and specified ranges are disclosed in the present application for use in various embodiments of the methods. Additionally, the aforementioned methods may further comprise centrifuging the isolated platelet rich plasma unit to provide a platelet rich plasma unit having separated layers of platelet poor plasma and platelet concentrate; and isolating the separated layer of platelet concentrate to provide a platelet concentrate unit. Such platelet concentrate units may further be pooled to achieve desired platelet quantities and/or to prepare the platelet concentrate(s) for pathogen inactivation.

In another aspect, the present disclosure provides a method of preparing a pooled platelet product, comprising: identifying a plurality of donated whole blood units according to one or more parameters selected from the group consisting of hematocrit, hemoglobin and donor gender; selecting a subset of whole blood units from the plurality of donated whole blood units, wherein each unit of the selected subset is within one of at least two specified ranges for at least one of the one or more parameters; centrifuging the selected subset of units under the same centrifugation conditions to provide each unit having a separated layer of platelet rich plasma; isolating the separated layer of platelet rich plasma to provide a platelet rich plasma unit; centrifuging the isolated platelet rich plasma unit to provide a platelet rich plasma unit having separated layers of platelet poor plasma and platelet concentrate; isolating the separated layer of platelet concentrate to provide a platelet concentrate unit; and pooling at least seven (e.g., seven, eight) isolated platelet concentrate units into one container to provide a pooled platelet product; and optionally, treating the pooled platelet product with a pathogen inactivation compound to inactivate pathogens, if present; and/or optionally, transferring the pooled platelet product into two storage containers to provide a double dose platelet product.

In another aspect, the present disclosure provides a method of preparing a pooled platelet product, comprising: identifying a plurality of donated whole blood units according donor gender; selecting a first subset of whole blood units from the plurality of donated whole blood units, wherein each unit of the first selected subset is the same donor gender; centrifuging the first selected subset of units under the same centrifugation conditions to provide each unit having a separated layer of platelet rich plasma; isolating the separated layer of platelet rich plasma to provide a platelet rich plasma unit; centrifuging the isolated platelet rich plasma unit to provide a platelet rich plasma unit having separated layers of platelet poor plasma and platelet concentrate; isolating the separated layer of platelet concentrate to provide a platelet concentrate unit from the first subset of whole blood units; selecting a second subset of whole blood units from the plurality of donated whole blood units, wherein each unit of the second selected subset is the same donor gender, and wherein the donor gender of the second selected subset is different from the donor gender of the first selected subset; centrifuging the second selected subset of units under the same centrifugation conditions to provide each unit having a separated layer of platelet rich plasma, wherein the centrifugation conditions for the second subset of whole blood units are different from the centrifugation conditions of the first subset of whole blood units; isolating the separated layer of platelet rich plasma to provide a platelet rich plasma unit; centrifuging the isolated platelet rich plasma unit to provide a platelet rich plasma unit having separated layers of platelet poor plasma and platelet concentrate; isolating the separated layer of platelet concentrate to provide a platelet concentrate unit from the second subset of whole blood units; pooling at least seven (e.g., seven, eight) isolated platelet concentrate units into one container to provide a pooled platelet product; and optionally treating the pooled platelet product with a pathogen inactivation compound to inactivate pathogens, if present; and/or optionally transferring the pooled platelet product into two storage containers to provide a double dose platelet product.

In case the platelet donor count is known, pre-selection of RDP's before pooling can be used to optimize platelet dose per RDP pool and to select RDP's for double dose production, in such instances where a double dose product is desired, for example:

compound to a unit of platelets. For example, pathogen inactivation may involve the addition of a low molecular weight compound that inactivates various pathogens, where a preferred method involves the addition of a photosensitizer that, when activated by illumination using light of suitable wavelengths, will inactivate a variety of pathogens that may be present. Two preferred methods currently developed include the addition of amotosalen or riboflavin to the platelets, with subsequent illumination with UV light. Other methods include illumination with UV light without addition of a photosensitizer, as well as illumination with other photoactive compounds, including psoralen derivatives other than amotosalen, isoalloxazines other than riboflavin, alloxazines, dyes such as phthalocyanines, phenothiazine dyes (e.g. methylene blue, azure B, azure C, thionine, toluidine blue), porphyrin derivatives (e.g. dihematoporphyrin ether, hematoporphyrin derivatives, benzoporphyrin derivatives, alkyl-substituted sapphyrin), and merocyanine 540 (Prodouz et al., Blood Cells 1992, 18(1):101-14; Sofer, Gail, BioPharm, August 2002). Other pathogen inactivation systems include, for example, those described in PCT publication numbers WO 2012071135; WO 2012018484; WO 2003090794; WO 2003049784; WO 1998018908; WO 1998030327; WO 1996008965; WO 1996039815; WO 1996039820; WO 1996040857; WO 1993000005; US patent application number US 20050202395; and U.S. Pat. Nos. 8,296,071 and 6,548,242, the disclosures of which are hereby incorporated by reference as they relate to pathogen inactivation in blood products. Where addition of a compound to the platelets is used for pathogen inactivation, whether the method requires illumination or not, in some

| Pool size | Average donor platelet count $\times 10^9$/L | Average Platelet dose | | | | |
|---|---|---|---|---|---|---|
| | | in WB collections (450 mL) $\times 10^{11}$ | In RDP pool (90% recovery) $\times 10^{11}$ | After pooling and filtration $\times 10^{11}$ | After Pathogen Inactivation $\times 10^{11}$ | Split product $\times 10^{11}$ |
| 5 | 200 | 4.5 in 2250 mL WB | 4.1 | 3.6 | 3.3 | na |
| 7 | 250 | 7.9 in 3150 mL WB | 7.1 | 6.4 | 5.7 | 2.9 |
| 8 | 230 | 8.3 in 3600 mL WB | 7.5 | 6.7 | 6.0 | 3.0 |

Pooling may be performed using techniques known in the art, such as using sterile connecting device and storage containers of sufficient size for pooled platelet products, as well as specifically designed pooling sets.

Pathogen Inactivation

Blood products, including platelet-containing blood products, may contain pathogens, or may be contaminated with pathogens during processing. As such, it is desirable to subject such blood products to a process in order to reduce the risk of transfusion-transmitted diseases. Various methods have been assessed to mitigate the risk of transfusion-associated disease transmission in platelet-containing blood products. Aside from screening and detection of pathogens and subsequent elimination of contaminated blood products, processes that incorporate treatments to inactivate pathogens (i.e., pathogen inactivation) that may be present are available. Ideally, such a process results in the inactivation of a broad range of pathogens such as viruses, bacteria and parasites that may be present in the blood product. In certain preferred embodiments, the methods of pathogen inactivation require addition of an amount of pathogen inactivation instances it is desirable to remove any residual pathogen inactivation compound or by-product thereof.

Methods for pathogen inactivation and removal of pathogen inactivation compound as described herein are applicable to any platelet units, whether the platelet units are prepared by the platelet rich plasma method or otherwise (e.g., apheresis, buffy coat preparation), including pooling of platelet rich plasma concentrates, or by any other method. These processes typically provide a unit of platelets that is either in about 85% to 100% plasma or has some amount of platelet additive solution added, typically in the range of 50 to 95% platelet additive solution, with the rest of the volume effectively being plasma, i.e. plasma in the range of about 5 to 50%. It is understood that a solution of pathogen inactivation compound can be added during the processing to inactivate pathogens, since pathogen inactivating compound is not typically combined in solid form, but is dissolved in a solution (for example, amotosalen is the HCl salt dissolved in a saline solution). As such, in some instances, when a platelet unit is designated as about 100% plasma, it is understood that this means no additional platelet additive solution is included in the platelet unit. If such plasma unit of platelets in about 100% plasma is treated for pathogen inactivation, some volume of the solution of pathogen inactivating compound will be included in the final product, as well as some volume of anticoagulant used in collecting the blood for isolation of platelets. While the plasma has been diluted partially with whatever amount of anticoagulant and solution that is used to contain the pathogen inactivating compound, the resulting unit of platelets including pathogen inactivation compound may be referred to as comprising about 100% plasma, or may be referred to as about 85 to 100% plasma (typically less than about 5 to 15% of the volume will comprise the solution used to deliver the pathogen inactivating compound). Platelet units can also be prepared with some amount of platelet additive solution, which is typically added after centrifuging the platelet unit to concentrate the platelets, removing a portion of the plasma from the supernatant, and adding the desired amount of platelet additive solution to the platelet unit. The platelet additive is added to provide the desired percentage of platelet additive solution. Such a unit of platelets is typically adjusted so the plasma content is about 5 to 50%, with the remainder of the solution being platelet additive solution, i.e. 50 to 95% platelet additive solution. When amounts of plasma and platelet additive solutions are described, it is understood that as with platelet units described as being in about 100% plasma, some volume of solution containing a pathogen inactivating compound may be included in the unit of platelets containing a pathogen inactivation compound. While the solution has been diluted partially with whatever amount of solution is used to contain the pathogen inactivating compound, it is understood that, for example, a platelet unit designated as comprising 35% plasma and 65% platelet additive solution may refer to relative amounts of plasma and platelet additive solution prior to the addition of a solution containing pathogen inactivation compound.

Some pathogen inactivation methods may require the use of a removal device, i.e. a device for reducing the concentration of pathogen inactivation compound, such as a small organic compound, e.g. platelet inactivation compound, and by-products thereof in a unit of platelets while substantially maintaining a desired biological activity of the platelets. Such a removal device is intended to be used in a batch mode, i.e. the device is placed in contact with the unit of platelets, and continued contact with the removal device, e.g. with shaking to allow essentially the entirety of the solution of platelets to come into contact with the removal device over time of contact, results in reducing the levels of pathogen inactivation compound. Such batch devices entail the use of an adsorbent particle that binds the pathogen inactivation compound, and can be used by either adding adsorbent particles directly to the platelet bag following illumination or transferring the platelets to a bag containing the adsorbent particles following illumination and the platelets are then agitated for a specified period of time with the unit of platelets contacting the removal device. While free adsorbent particles may be used as a removal device, such particles may be contained within a mesh pouch, such as a polyester or nylon mesh pouch, which allows for contact of the platelet solution with the adsorbent particles while containing the particles within the pouch. Alternatively, the adsorbent particles may be immobilized within a matrix, where the immobilized matrix can reside directly in the blood bag used for batch removal, or may be similarly contained within a mesh pouch. In some instances, the removal device comprises porous adsorbent particles in an amount sufficient to reduce the pathogen inactivation compound to below a desired concentration, wherein the adsorbent particles have an affinity for the pathogen inactivation compound, where it is understood such adsorbent particle can be selected to best adsorb the compound or compounds to be removed, with minimal effect on components that should not be removed or damaged by contact with the adsorbent particle. A variety of adsorbent particles are known, including generally particles made from any natural or synthetic material capable of interacting with compounds to be removed, including particulates made of natural materials such as activated carbon, silica, diatomaceous earth, and cellulose, and synthetic materials such as hydrophobic resins, hydrophilic resins or ion exchange resins. Such synthetic resins include, for example, carbonaceous materials, polystyrene, polyacrylic, polyacrylic ester, cation exchange resin, and polystyrene-divinylbenzene. Detailed description of such removal devices suitable for use in the methods as described herein can be found in PCT publication numbers WO 1996040857, WO 1998030327, WO 1999034914, and WO 2003078023, the disclosures of which are hereby incorporated by reference with respect to the discussion of such removal devices and the adsorbent particles and other materials used to prepare such devices. Exemplary adsorbent particles include, but are not limited to, Amberlite (Rohm and Haas) XAD-2, XAD-4, XAD-7, XAD-16, XAD-18, XAD-1180, XAD-1600, XAD-2000, XAD-2010; Amberchrom (Toso Haas) CG-71m, CG-71c, CG-161m, CG161c; Diaion Sepabeads (Mitsubishi Chemicals) HP20, SP206, SP207, SP850, HP2MG, HP20SS, SP20MS; Dowex (Dow Chemical) XUS-40285, XUS-40323, XUS-43493 (also referred to as Optipore V493 (dry form) or Optipore L493 (hydrated form)), Optipore V503, Optipore SD-2; Hypersol Macronet (Purolite) MN-100, MN-102, MN-150, MN-152, MN-170, MN-200, MN-202, MN-250, MN-252, MN-270, MN-300, MN-400, MN-500, MN-502, Purosorb (Purolite) PAD 350, PAD 400, PAD 428, PAD 500, PAD 550, PAD 600, PAD 700, PAD 900, and PAD 950. The material used to form the immobilized matrix comprises a low melting polymer, such as nylon, polyester, polyethylene, polyamide, polyolefin, polyvinyl alcohol, ethylene vinyl acetate, or polysulfone. In one example, the adsorbent particles immobilized in a matrix are in the form of a sintered medium. While it is understood that the methods and devices described herein encompass removal devices as are known in the art, such methods and devices may be exemplified using the removal device of an amotosalen inactivated platelet product as is commercially available. Such a removal device comprises Hypersol Macronet MN-200 adsorbent contained within a sintered matrix, where the sintered matrix comprises PL2410 plastic as a binder. In one instance, the removal device comprises Hypersol Macronet MN-200 adsorbent in a sintered matrix comprising PL2410, wherein the Hypersol Macronet MN-200 is in an amount of about 5 g dry weight equivalent.

As various resins may require different processing when used to make the removal devices useful in the methods and devices as described herein, comparison of amounts of adsorbent resins described herein, unless otherwise indicated, are comparison of the dry weight of the resin. For example, the resins are dried to <5% water prior to processing, and the equivalent of the dry weight of adsorbent is used in comparing amounts of resin in use. For example, Hypersol Macronet MN-200 is processed to stabilize the adsorbent, or what is typically referred to as wetting the adsorbent, so as to be directly usable upon contact with a platelet unit. Such a wetted sample may include, for example, about 50% glycerol or other suitable wetting agent. In some embodiments, the adsorbent resin is a polystyrene-divinylbenzene resin. In some embodiments, the polystyrene-divinylbenzene resin is Hypersol Macronet MN-200. In some embodiments, the adsorbent is contained within a sintered matrix, wherein the sintered matrix comprises PL2410 binder. In some embodiments, Hypersol Macronet MN-200 adsorbent is contained within a sintered matrix to provide a removal device.

Regardless of how platelets are collected, prepared and pooled the processing of platelet products typically involves storage in a suitable container, such as a suitable blood bag, with agitation. Agitation is a necessary component of storage in order to avoid aggregate formation and maintain adequate oxygen levels, thereby providing desirable platelet function for use in transfusion to patients in need thereof. As such, platelets should be stored at a temperature of between 20 and 24° C. with continuous agitation. In practice, platelets are stored with commercially available platelet shakers (agitators), at ideally about 60 to 75 cycles per minute. For example, such shakers include, but are not limited to, various Helmer models; Forma Scientific 4720; Thermoline TPS-16; Unimeditrek Platelet Agitator or Yorco Platelet Agitator; Nicosound Electronics; Lmb Platelet Agitator; and TANCO Platelet Agitator.

Platelet Characterization

Platelets (e.g., platelet rich plasma, platelet concentrate) prepared from whole blood according to the methods disclosed herein may be characterized by a variety of qualitative and/or quantitative methods known in the art. Such characteristics may include, for example, red blood cell (RBC) contamination, lipid contamination, platelet aggregation, platelet recovery, platelet viability, swirling pattern, potency, platelet survival, morphology, white blood cell (WBC) contamination, functional activity, activation markers, pH, concentration of growth factors and icterus.

Contamination of platelets with RBC may be determined by any of several methods known in the art, such as for example, visual inspection for color indicative of RBC contamination. More specifically, RBC contamination above a certain level (e.g., >400 RBC/mL), results in platelets that exhibit discoloration from a light pink/salmon, reddish-orange color tinge to a marked red discoloration, which may be compared to standard visual inspection charts. Lipid contamination (e.g., lipemia) may similarly be determined by visual methods, with increased opacity, 'milky' white appearance, large lipid particles that include lipoproteins and chylomicrons, and the like. Platelet aggregation may be determined visually and/or using any of a number of techniques and devices, such as for example, platelet aggregometry, optical aggregometers, lumi-aggregometers, light transmission aggregometry or turbidometric aggregometry. White blood cell contamination may be determined manually, such as for example performing a leukocyte count (e.g., using a Neubauer counting chamber). Platelet morphology may be visually inspected at different levels of resolution, including with a discs vs. spheres estimate, and the presence of different morphological forms may be quantitated. The functionality can be estimated by platelet response to osmotic stress and by the extent of agonist-induced shape change. Aggregation to increasing concentrations of physiologic agonists such as ADP, collagen, epinephrine, or to dual agonist combinations of ADP/epinephrine and ADP/collagen will give an idea of the responsiveness of the platelet. Platelet serotonin uptake and agonist-induced serotonin secretion and agonist-induced expression of platelet activation markers such as GMP-140, will also evaluate the platelet physiologic response. Additionally, platelet cellular levels of ATP, glucose, and lactate provide an indication of platelet performance. Activation of platelets is associated with surface expression of the various surface antigens, such as for example, GMP-140 (P-selectin, CD 62), CD 63, and the active form (fibrinogen-binding) of GPIIb/IIIa (detected by PAC-1). Thromboglobulin and/or Platelet Factor 4 released by activated platelets into the medium are platelet-specific proteins and can be measured as indicators of platelet activation. Platelet Factor 3 activity (procoagulant surface for binding clotting proteins) also becomes increased with platelet activation.

Platelets (e.g., pathogen inactivated platelets) prepared by the methods described herein may also be used for the preparation of other platelet derived products, such as for example, platelet lysate. In such uses, the pathogen inactivated platelet product does not necessarily need to be suitable for infusion, and typically will not be used for infusion, but rather can be processed by methods to provide the desired platelet derived product. For example, platelet lysate can be prepared by various methods, such as treating the pathogen inactivated platelets with one or more freeze thaw cycles. Platelet lysate has a variety of uses, including wound healing, and in cell culturing, for example as an adjuvant in the culturing of stem cells. Additional discussion of the preparation and use of platelet lysates can be found, for example, in PCT publications WO 2009087560, WO 2010064267, WO 2010033605, WO 2012085910, and WO 2013042095, the disclosures of which are herein incorporated by reference as it relates to the preparation of platelet lysate, including pathogen inactivated platelet lysate, and uses thereof.

The invention is illustrated further by the following examples, which are not to be construed as limiting the invention in scope or spirit to the specific procedures described in them.

EXAMPLES

Example 1

Platelet Preparation with a Selected Subset of Units Based on One Parameter

Analysis of hematocrit levels for a population of random whole blood donors indicates different average levels of hematocrit between female (about 0.42 L/L) and male (about 0.46 L/L) donors (FIG. 1). This difference in properties between the female and male donor provides an opportunity to evaluate the potential for improved methods incorporating subset selection based on gender when preparing platelet containing products, as provided in the following example.

Female Donor Subset

RDP platelet concentrates were prepared by the PRP method. From whole blood donations obtained using standard phlebotomy (e.g., venipuncture) procedures, a selected subset of whole blood units limited to only those from female donors was processed. Whole blood unit donations in 450 mL blood bags (±10% volume) were centrifuged within 8 hours of collection using a JOUAN KR4i centrifuge equipped with a RP6 rotor for processing 12 whole blood units per run. For the initial centrifugation, the following settings were used: 1590×g, for 5 min, with brake 2, with acceleration 6, and temperature at 22° C. Platelet rich plasma was separated from the red blood cells using a Compomat G-5, followed by a secondary centrifugation of the PRP in the same centrifuge; with the following settings: 4778×g, for 8 min, with brake 5, with acceleration 6, and temperature 22° C. The plasma layer on top of the platelet concentrate was removed by expressing using the Compomat G-5, to leave a final platelet concentrate volume of about 60 mL for the RDP. The platelet concentrates were stored in a platelet incubator with agitation at about 22° C.

Within 36 hours of preparing the platelet concentrates, 5 ABO matched RDP's of approximately 60 mL were pooled in a standard 600 mL transfer container (Grifols, Spain) by using a sterile connection device. In total, 24 female RDP pools were prepared from randomly selected whole blood donors. Routine quality control data across random donors that include both male and female shows a platelet dose average of $0.8 \times 10^{11}$ platelets per RDP concentrate. In this experiment, the subset of female donations shows a higher platelet dose average of $1.0 \times 10^{11}$ platelets per RDP concentrate. The centrifugation settings were not further optimized.

Male and Female Donor Subsets

In a separate study, another PRP processing method for platelets currently used by a blood center as standard procedure for all whole blood units (i.e., male and female) was evaluated for specific male and female donor subsets. Whole blood unit donations of about 470 mL were collected, initial platelet counts were determined from a sample pouch to allow calculation of percent recovery post-processing, and the whole blood units were centrifuged within 8 hours of collection using a Sorvall RC3 centrifuge equipped with a 6000H rotor for processing 6 whole blood units per run. For the initial centrifugation, the following settings were used: 2710×g (3050 rpm), for 4 min, with brake 100, and temperature at 22° C. Platelet rich plasma was separated from the red blood cells using a Compomat G-5, followed by a secondary centrifugation of the PRP in the same centrifuge; with the following settings: 2983×g (3200 rpm), for 12 min, with brake 200, and temperature 22° C. The plasma layer on top of the platelet concentrate was removed by expressing using the Compomat G-5, to leave a final platelet concentrate volume of about 65 mL for the RDP platelet concentrate. Platelet counts for the PRP and RDP platelet concentrates were determined and compared with the initial whole blood platelet counts to determine recovery percentages. Plasma (FFP) recovery was also determined.

As shown in the following table, the standard PRP method provided very different platelet recovery percentages for male versus female donor units, with the male donor units yielding an average recovery of 92.5% and 86.1% for PRP and platelet concentrate, respectively, and the female donor units yielding significantly lower average recoveries of 78.0% and 75.7% for PRP and platelet concentrate, respectively.

separated from the red blood cells using a Compomat G-5, followed by a secondary centrifugation of the PRP in the same centrifuge; with the following settings: 2983×g (3200 rpm), for 12 min, with brake 200, and temperature 22° C., for both the male and female subsets. The plasma layer on top of the platelet concentrate was removed, to leave a final platelet concentrate volume of about 65 mL for the RDP platelet concentrate. Platelet counts for the PRP and RDP platelet concentrates were determined as above, with the recovery percentages shown in the above table. Plasma recovery was also determined. As shown in the table, the male PRP method provided improved platelet recovery percentages compared to the standard procedure for male donor units of 96.7% and 89.4% for PRP and platelet concentrate, respectively. In addition, the female PRP method provided even greater improvement in platelet recovery compared to the standard procedure for female donor units of 95.4% and 86.9% for PRP and platelet concentrate, respectively. Similar improvement levels were not observed for male donor units processed using the female PRP method, or the female donor units processed using the male PRP method.

Hematocrit Subsets

In another study, PRP methods for platelets are implemented for different donor subsets based on hematocrit measurement. Whole blood unit donations are collected as above, subjected to one or more measurements including hematocrit (e.g., hematocrit and whole blood volume, total blood count and/or initial platelet counts), and the whole blood units are centrifuged within 8 hours of collection using a Sorvall RC3 centrifuge equipped with a 6000H rotor for processing 6 whole blood units per run. Whole blood units are separated into two groups for platelet preparation: a first group with units having hematocrit less than about 43.5% (e.g., <43.5%, about 38.0% to about 43.5%, about 38.0% to about 43.0%) and a second group with units having hematocrit greater than about 43.5% (e.g., >43.5%, about 43.5% to about 50.0%, about 44.0% to about 50.0%).

More specifically, for the initial centrifugation in the example, the following settings are used for the donor subset with hematocrit >43.5%: 1000×g (1850 rpm), for 7 min 46 sec ($1.6 \times 10^7$ rad$^2$/s), with brake 300, and for the donor subset with hematocrit <43.5%: 1000×g (1850 rpm), for 10 min 44 sec ($1.9 \times 10^7$ rad$^2$/s), with brake 300. Platelet rich plasma is separated from the red blood cells using a Compomat G-5, followed by a secondary centrifugation of the PRP in the same centrifuge; with the following settings: 2983×g (3200 rpm), for 12 min, with brake 200, and temperature 22° C., for both hematocrit level subsets. The

| Platelet and Plasma Recovery (%) Using Standard and Gender Selected Subset Procedures | | | | | | | | | |
|---|---|---|---|---|---|---|---|---|---|
| | Standard PRP procedure | | | Male PRP Procedure | | | Female PRP Procedure | | |
| Gender | PRP | RDP | FFP | PRP | RDP | FFP | PRP | RDP | FFP |
| Male | 92.5% | 86.1% | 80.9% | 96.7% | 89.4% | 83.1% | 85.0% | na | 71.5% |
| Female | 78.0% | 75.7% | 91.3% | 90.5% | 84.1% | 85.0% | 95.4% | 86.9% | 89.9% |

Therefore, separate PRP processing methods were identified for male and female donor units for use in the subset selection methods based on gender, as provided herein. For the initial centrifugation, the following settings were used for the male donor subset: 1000×g (1850 rpm), for 7 min 46 sec ($1.6 \times 10^7$ rad$^2$/s), with brake 300, and for the female donor subset: 1000×g (1850 rpm), for 10 min 44 sec ($1.9 \times 10^7$ rad$^2$/s), with brake 300. Platelet rich plasma was plasma layer on top of the platelet concentrate is removed, to leave a final platelet concentrate volume of about 65 mL for the RDP platelet concentrate. Platelet counts for the PRP and RDP platelet concentrates are determined as above.

Hemoglobin Subsets

In another study, PRP methods for platelets are implemented for different donor subsets based on hemoglobin measurement. Whole blood unit donations are collected as above, subjected to one or more measurements including hemoglobin (e.g., hemoglobin and whole blood volume, total blood count and/or initial platelet counts), and the whole blood units are centrifuged within 8 hours of collection using a Sorvall RC3 centrifuge equipped with a 6000H rotor for processing 6 whole blood units per run. Whole blood units are separated into two groups for platelet preparation: a first group with units having hemoglobin less than about 15.0 g/dL (e.g., <15 g/dL) and a second group with units having hemoglobin greater than about 15 g/dL (e.g., >15 g/dL).

More specifically, for the initial centrifugation in the example, the following settings are used for the donor subset with hemoglobin >15 g/dL: 1000×g (1850 rpm), for 7 min 46 sec ($1.6 \times 10^7$ rad$^2$/s), with brake 300, and for the donor subset with hemoglobin <15 g/dL: 1000×g (1850 rpm), for 10 min 44 sec ($1.9 \times 10^7$ rad$^2$/s), with brake 300. Platelet rich plasma is separated from the red blood cells using a Compomat G-5, followed by a secondary centrifugation of the PRP in the same centrifuge; with the following settings: 2983×g (3200 rpm), for 12 min, with brake 200, and temperature 22° C., for both hemoglobin level subsets. The plasma layer on top of the platelet concentrate is removed, to leave a final platelet concentrate volume of about 65 mL for the RDP platelet concentrate. Platelet counts for the PRP and RDP platelet concentrates are determined as above.

Example 2

Platelet Preparation Based on Two Parameters and Four Selected Subsets

Subsets of whole blood units may be selected based on two parameters for the preparation of platelet containing products. FIG. 2 illustrates four subsets based on a combination of whole blood volume and hematocrit. The first subset comprises those whole blood units with a volume in the range of 404-450 mL and hematocrit in the range of 0.38-0.435 L/L. The second subset comprises those whole blood units with a volume in the range of 405-450 mL and hematocrit in the range of 0.44-0.50 L/L. The third subset comprises those whole blood units with a volume in the range of 455-495 mL and hematocrit in the range of 0.38-0.435 L/L. The fourth subset comprises those whole blood units with a volume in the range of 455-495 mL and hematocrit in the range of 0.44-0.50 L/L.

Each whole blood unit is centrifuged within 8 hours of collection using a JOUAN KR4i centrifuge equipped with a RP6 rotor for processing 12 whole blood units per run. Optimal centrifugation conditions for each of the subsets are identified, for example among "g", time, brake setting, acceleration setting, and temperature. Platelet rich plasma is separated from the red blood cells using a Compomat G-5, followed by a secondary centrifugation of the PRP in the same centrifuge; with settings appropriate for the platelet concentration step (e.g., 4778×g, for 8 min, with brake 5, with acceleration 6, and temperature 22° C.). The plasma layer on top of the platelet concentrate is removed by expressing using the Compomat G-5, to leave a final platelet concentrate volume of about 60 mL for the RDP.

Example 3

Platelet Preparation Based on Two Parameters and Two Selected Subsets

Subsets of whole blood units may be selected based on two parameters for the preparation of platelet containing products. FIG. 3 illustrates two subsets based on a combination of whole blood volume and hematocrit. The first subset comprises those whole blood units with a volume in the range of 420-480 mL and hematocrit in the range of 0.38-0.435 L/L. The second subset comprises those whole blood units with a volume in the range of 420-480 mL and hematocrit in the range of 0.44-0.50 L/L.

Each whole blood unit is centrifuged within 8 hours of collection using a JOUAN KR4i centrifuge equipped with a RP6 rotor for processing 12 whole blood units per run. Optimal centrifugation conditions for each of the subsets are identified, for example among "g", time, brake setting, acceleration setting, and temperature. Platelet rich plasma is separated from the red blood cells using a Compomat G-5, followed by a secondary centrifugation of the PRP in the same centrifuge; with settings appropriate for the platelet concentration step (e.g., 4778×g, for 8 min, with brake 5, with acceleration 6, and temperature 22° C.). The plasma layer on top of the platelet concentrate is removed by expressing using the Compomat G-5, to leave a final platelet concentrate volume of about 60 mL for the RDP.

Example 4

Preparation of Pooled Platelet Concentrates

The aforementioned methods and results provide a means to achieve improved preparation and pooling methods for platelet concentrates (e.g., RDP platelet concentrates), with resulting pooled platelet concentrate products of a desired platelet dose level (e.g., at least $3 \times 10^{11}$ platelets).

For example, single dose pooled platelet preparations in 100% plasma and comprising at least $3 \times 10^{11}$ platelets are obtained, for example, by pooling 4 or 5 RDP platelet concentrates prepared as described above, and as follows. In the case of pooling 4 platelet concentrates, the platelet concentrates may be prepared, for example, in a final plasma volume of about 65-70 mL per unit, followed by combining the 4 units to produce a single dose pooled preparation of about 270 mL. In the case of pooling 5 platelet concentrates, the platelet concentrates may be prepared, for example, in a final plasma volume of about 50-60 mL per unit, followed by combining the 5 units to produce a single dose pooled preparation of about 270 mL.

Alternatively, single dose pooled platelet preparations in about 35% plasma and 65% platelet additive solution (PAS) and comprising at least $3 \times 10^{11}$ platelets are obtained, for example, by pooling 4 or 5 RDP platelet concentrates prepared as described above, and as follows. In the case of pooling 5 platelet concentrates, the platelet concentrates may be prepared, for example, in a final plasma volume of about 20-35 mL per unit, followed by combining the 5 units together with about 200 mL of PAS to produce a single dose pooled preparation of about 340 mL.

Further, double dose pooled platelet preparations in a desired suspension medium (e.g., 100% plasma, 35% plasma/65% PAS) and comprising sufficient platelets for two platelet units with each of the two units containing at least about $3 \times 10^{11}$ platelets are obtained, for example, by pooling 7 or 8 RDP platelet concentrates prepared as described above, and as follows. In the case of pooling 7 platelet concentrates in 100% plasma, the platelet concentrates may be prepared, for example, in a final plasma volume of about 60 mL per unit, followed by combining the 7 units to produce a pooled preparation of at least $6 \times 10^{11}$ platelets in about 420 mL that is then divided into two single dose storage containers, whereby each of the two platelet units contain at least $3 \times 10^{11}$ platelets. In the case of pooling 8 platelet concentrates in 100% plasma, the platelet concentrates may be prepared, for example, in a final plasma volume of about 50 mL per unit, followed by combining the 8 units to produce a pooled preparation of at least $6 \times 10^{11}$ platelets in about 400 mL that is then divided into two single dose storage containers, whereby each of the two platelet units contain at least $3 \times 10^{11}$ platelets.

For example, pooling 7 platelet concentrates prepared as described above using donor gender selection, in various male and female unit combinations, and with an estimated average platelet amount as indicated below provides opportunity to produce a pooled platelet preparation (e.g., double dose) of at least about $6 \times 10^{11}$ platelets, which may be subjected to pathogen inactivation as an optional step and divided into two individual dose storage containers.

Exemplary combinations of RDP from male and female donor units to prepare a 7 unit pool[a]

| | # male | | | | | | | |
|---|---|---|---|---|---|---|---|---|
| | 0 | 1 | 2 | 3 | 4 | 5 | 6 | 7 |
| | # female | | | | | | | |
| | 7 | 6 | 5 | 4 | 3 | 2 | 1 | 0 |
| Male[b] | 0.0 | 0.8 | 1.7 | 2.5 | 3.4 | 4.2 | 5.0 | 5.9 |
| Female[b] | 7.0 | 6.0 | 5.0 | 4.0 | 3.0 | 2.0 | 1.0 | 0.0 |
| Total[b] | 7.0 | 6.8 | 6.7 | 6.5 | 6.4 | 6.2 | 6.0 | 5.9 |

[a]Based on estimated average platelet count of $.84 \times 10^{11}$ (male) and $1 \times 10^{11}$ (female)
[b]Platelet dose $\times 10^{11}$ Alternatively, for example, pooling 8 platelet concentrates prepared as described above using donor gender selection, in various male and female unit combinations, and with an estimated average platelet amount as indicated below provides opportunity to produce a pooled platelet preparation (e.g., double dose) of at least about $6 \times 10^{11}$ platelets, which may be pathogen inactivated and divided into two individual dose storage containers.

Exemplary combinations of RDP from male and female donor units to prepare a 8 unit pool[a]

| | # male | | | | | | | | |
|---|---|---|---|---|---|---|---|---|---|
| | 0 | 1 | 2 | 3 | 4 | 5 | 6 | 7 | 8 |
| | # female | | | | | | | | |
| | 8 | 7 | 6 | 5 | 4 | 3 | 2 | 1 | 0 |
| Male[b] | 0.0 | 0.8 | 1.7 | 2.5 | 3.4 | 4.2 | 5.0 | 5.9 | 6.7 |
| Female[b] | 8.0 | 7.0 | 6.0 | 5.0 | 4.0 | 3.0 | 2.0 | 1.0 | 0.0 |
| Total[b] | 8.0 | 7.8 | 7.7 | 7.5 | 7.4 | 7.2 | 7.0 | 6.9 | 6.7 |

[a]Based on estimated average platelet count of $.84 \times 10^{11}$ (male) and $1 \times 10^{11}$ (female)
[b]Platelet dose $\times 10^{11}$ The pooled platelet concentrates are preferably treated by a pathogen inactivation process, such as for example treatment with a pathogen inactivation compound, for which several are available commercially (e.g., INTERCEPT® Blood System, Cerus Corporation). The platelet concentrates (e.g., pooled platelet concentrates) also may be optionally subjected to a leukoreduction step, such as for example using a commercially available leukoreduction filter (e.g., Platelet filter, Haemonetics, Braintree, Mass.)

In one example of double dose platelet preparation, pools of 8 ABO-identical, whole blood-derived RDPs ($53.8 \pm 0.8$ mL) were generated by pooling within 36 hours of collection into a standard 600 mL transfer container (n=7 pools), and leukoreduction by filtration. The pools comprised mixtures of both male and female donor derived RDPs prepared by the PRP method following gender selection and using different centrifugation conditions for each donor gender as described above for greater platelet yield. Four pools each consisted of RDP from 4 male donor units and 4 female donor units, two pools each consisted of RDP from 5 male donor units and 3 female donor units, and one pool consisted of RDP from 6 male donor units and 2 female donor units (see following table).

| Pool # | Male units | Female units | Platelet dose/product |
|---|---|---|---|
| 1 | 4 | 4 | $3.1 \times 10^{11}$ |
| 2 | 5 | 3 | $3.8 \times 10^{11}$ |
| 3 | 4 | 4 | $3.8 \times 10^{11}$ |
| 4 | 6 | 2 | $3.2 \times 10^{11}$ |
| 5 | 4 | 4 | $3.8 \times 10^{11}$ |
| 6 | 5 | 3 | $3.1 \times 10^{11}$ |
| 7 | 4 | 4 | $3.5 \times 10^{11}$ |

The resulting mean volume across pools was $402 \pm 5$ mL and the mean platelet count was $1826 \pm 193 \times 10^9$/L, with a mean total platelet amount of $7.3 \times 10^{11}$ for the double dose pools. The double dose RDP pools were subjected to pathogen inactivation using the INTERCEPT Blood System, with 150 µM amotosalen and 3 J/cm$^2$ UVA, split into two platelet doses in separate containers for transfusion, and stored at 20-24° C. with flatbed agitation for 7 days. In vitro assays to assess platelet quality were performed on all pools on days 1 (pre-treatment), 2, 5 and 7.

As shown in the above table, the resulting platelet doses per product obtained from each RDP pool were 3.1, 3.8, 3.8, 3.2, 3.8, 3.1 and $3.5 \times 10^{11}$, with a mean platelet dose of $3.5 \pm 0.3 \times 10^{11}$ and mean volume of 195.3 mL per product, after splitting the double dose platelet preparations into two individual storage bags. The pH (22° C.) of the pools remained stable over 7 days of storage (mean $6.8 \pm 0.1$) with a platelet swirl rating of 2-3 for all pools. Additionally, all pools showed active metabolism with maintained pO$_2$ levels ($121 \pm 17$ mm Hg) and adequate residual energy source (glucose, $176 \pm 8$ mg/dL).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Wherever an open-ended term is used to describe a feature or element, it is specifically contemplated that a closed-ended term can be used in place of the open-ended term without departing from the spirit and scope of the disclosure. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the description and does not pose a limitation on the scope of the description unless otherwise claimed. No language in the specification should be construed as indicating any non-claimed element as essential to the practice of the methods disclosed herein.

Preferred embodiments are described herein. Variations of those preferred embodiments may become apparent to those working in the art upon reading the foregoing description. It is expected that skilled artisans will be able to employ such variations as appropriate, and practice the methods described herein otherwise than as specifically described herein. Accordingly, the methods described herein include all modifications and equivalents of the subject matter recited in the claims appended hereto as permitted by applicable law. Moreover, any combination of the above-described elements in all possible variations thereof is encompassed by the description unless otherwise indicated herein or otherwise clearly contradicted by context.

What is claimed is:

1. A method of preparing a platelet product comprising:
   a) identifying a plurality of donated whole blood units according to one or more parameters selected from the group consisting of hematocrit, hemoglobin, donor gender, whole blood volume, packed cell volume and platelet count;
   b1) selecting a first subset of whole blood units from the plurality of donated whole blood units within a first specified range of at least two specified ranges for a given parameter of the one or more parameters; and
   b2) selecting a second subset of whole blood units from the plurality of donated whole blood units within a second specified range of the at least two specified ranges for the given parameter; and
   c) centrifuging the first selected subset of whole blood units and the second selected subset of whole blood units under different centrifugation conditions to provide each whole blood unit having a separated layer of platelet rich plasma; and
   d) isolating the separated layer of platelet rich plasma from each whole blood unit to provide platelet rich plasma units.

2. The method of claim 1, comprising identifying the plurality of donated whole blood units according to two or more said parameters.

3. The method of claim 1, wherein the at least two specified ranges for a parameter are non-overlapping ranges.

4. The method of claim 1, wherein the one or more parameters include hematocrit.

5. The method of claim 1, wherein the one or more parameters include hemoglobin.

6. The method of claim 1, wherein the one or more parameters include donor gender.

7. The method of claim 1, wherein the one or more parameters include whole blood volume.

8. The method of claim 1, wherein each whole blood unit of the selected subset of whole blood units is within the same specified range for two or more of said parameters.

9. The method of claim 8, wherein the two or more parameters include hematocrit and donor gender.

10. The method of claim 8, wherein the two or more parameters include either:
    donor gender and whole blood volume; or
    donor gender and hemoglobin.

11. The method of claim 1, wherein the specified range for the parameter in the first selected subset of whole blood units or the second selected subset of whole blood units is narrower than the range for the same parameter in the plurality of donated whole blood units.

12. The method of claim 1, wherein the specified range for the parameter in the first selected subset of whole blood units or the second selected subset of whole blood units is narrower than the range for the same parameter for donated whole blood that meets the acceptance criteria of a regulatory agency or accrediting organization for donated whole blood.

13. The method of claim 12, wherein the specified range for the parameter in the first selected subset of whole blood units or the second selected subset of whole blood units is narrower than the range for the same parameter for donated whole blood that meets the acceptance criteria of the U.S. Food and Drug Administration (FDA) or the AABB .

14. The method of claim 1, further comprising:
    e) centrifuging the isolated platelet rich plasma units to provide platelet rich plasma units having separated layers of platelet poor plasma and platelet concentrate; and
    f) isolating the separated layers of platelet concentrate to provide platelet concentrate units.

15. A method of preparing a platelet product, comprising:
    a) identifying a plurality of donated whole blood units according to donor gender;
    b) selecting a first subset of whole blood units from the plurality of donated whole blood units, wherein each whole blood unit of the first selected subset is the same donor gender;
    c) centrifuging the first selected subset of whole blood units under the same centrifugation conditions to provide each whole blood unit having a separated layer of platelet rich plasma;
    d) isolating the separated layer of platelet rich plasma to provide a platelet rich plasma unit;
    e) centrifuging the isolated platelet rich plasma unit to provide a platelet rich plasma unit having separated layers of platelet poor plasma and platelet concentrate;
    f) isolating the separated layer of platelet concentrate to provide a platelet concentrate unit from the first subset of whole blood units;
    g) selecting a second subset of whole blood units from the plurality of donated whole blood units, wherein each whole blood unit of the second selected subset is the same donor gender, and wherein the donor gender of the second selected subset is different from the donor gender of the first selected subset;
    h) centrifuging the second selected subset of whole blood units under the same centrifugation conditions to provide each whole blood unit having a separated layer of platelet rich plasma, wherein the centrifugation conditions for the second subset of whole blood units are different from the centrifugation conditions of the first subset of whole blood units;
    i) isolating the separated layer of platelet rich plasma to provide a platelet rich plasma unit;
    j) centrifuging the isolated platelet rich plasma unit to provide a platelet rich plasma unit having separated layers of platelet poor plasma and platelet concentrate; and
    k) isolating the separated layer of platelet concentrate to provide a platelet concentrate unit from the second subset of whole blood units.

16. The method of claim 14, wherein the isolated platelet concentrate unit further comprises donor plasma.

17. The method of claim 14, further comprising adding an additive solution to the isolated platelet concentrate unit.

18. The method of claim 14, further comprising pooling two or more of the isolated platelet concentrate units into one container to provide a pooled platelet product.

19. The method of claim 1, further comprising treating with a pathogen inactivation compound to inactivate pathogens, if present.

20. The method of claim 19, wherein the pathogen inactivation compound is a photoactive pathogen inactivation compound selected from the group consisting of a psoralen, an isoalloxazine, an alloxazine, a phthalocyanine, a phenothiazine, a porphyrin, and merocyanine 540.

21. The method of claim 20, wherein the pathogen inactivation compound is a psoralen.

22. The method of claim 21, wherein the pathogen inactivation compound is amotosalen.

23. The method of claim 6, wherein the specified range for donor gender in the selected subset of whole blood units is 100% female donors.

24. The method of claim 6, wherein the specified range for donor gender in the selected subset of whole blood units is 100% male donors.

25. The method of claim 14, wherein the isolated platelet concentrate unit comprises about $0.1 \times 10^{11}$ to about $2.2 \times 10^{11}$ platelets.

26. The method of claim 14, wherein the isolated platelet concentrate unit has a volume of about 45-80 mL.

27. The method of claim 14, wherein the isolated platelet concentrate unit has a volume of about 15-45 mL.

28. The method of claim 14, wherein the isolated platelet concentrate unit has a volume of less than about 5 mL.

29. The method of claim 16, wherein the donor plasma is an amount of remaining plasma from the platelet rich plasma unit.

30. The method of claim 18, comprising pooling 3-6 isolated platelet concentrate units.

31. The method of claim 18, comprising pooling 7-10 isolated platelet concentrate units.

* * * * *